(12) United States Patent
Littrup et al.

(10) Patent No.: US 8,376,946 B2
(45) Date of Patent: Feb. 19, 2013

(54) METHOD AND APPARATUS FOR COMBINED DIAGNOSTIC AND THERAPEUTIC ULTRASOUND SYSTEM INCORPORATING NONINVASIVE THERMOMETRY, ABLATION CONTROL AND AUTOMATION

(75) Inventors: Peter J. Littrup, Bloomfield Hills, MI (US); Nebojsa Duric, Albuquerque, NM (US); Earle Holsapple, III, Grosse Pointe Farms, MI (US)

(73) Assignee: Barbara Ann Karamanos Cancer Institute, Detroit, MI (US)

( * ) Notice: Subject to any disclaimer, the term of this patent is extended or adjusted under 35 U.S.C. 154(b) by 2324 days.

(21) Appl. No.: 10/440,427

(22) Filed: May 16, 2003

(65) Prior Publication Data

US 2004/0030227 A1 Feb. 12, 2004

Related U.S. Application Data

(63) Continuation-in-part of application No. 10/323,354, filed on Dec. 18, 2002, now Pat. No. 7,285,092, and a continuation-in-part of application No. 10/323,467, filed on Dec. 18, 2002, now Pat. No. 6,984,210.

(60) Provisional application No. 60/381,022, filed on May 16, 2002.

(51) Int. Cl.
*A61B 8/00* (2006.01)
(52) U.S. Cl. ........ 600/437; 600/438; 600/439; 600/485; 601/2; 601/3; 606/28; 606/41
(58) Field of Classification Search .................. 600/410, 600/407, 427, 437, 438, 439, 485; 424/9.321, 424/9.5; 601/2, 3; 606/28, 41
See application file for complete search history.

(56) References Cited

U.S. PATENT DOCUMENTS

| 3,154,067 A | 10/1964 | Stenstrom et al. |
| 3,881,466 A | 5/1975 | Wilcox |
| 3,886,489 A | 5/1975 | Jones |
| 4,028,934 A | 6/1977 | Sollish |
| 4,059,010 A | 11/1977 | Sachs |
| 4,075,883 A | 2/1978 | Glover |
| 4,105,018 A | 8/1978 | Greenleaf et al. |

(Continued)

FOREIGN PATENT DOCUMENTS

| AU | A-34432/95 | 2/1996 |
| CA | 2324602 A | 9/1999 |

(Continued)

OTHER PUBLICATIONS

Fjield et al, A parametric study of the concentric-ring transducer design for MRI guided ultrasound surgery, Aug 1996, J. Acoust. Soc. America 100 (2) Pt. 1.*

(Continued)

*Primary Examiner* — Unsu Jung
*Assistant Examiner* — Joel Lamprecht
(74) *Attorney, Agent, or Firm* — Jeffrey Schox

(57) ABSTRACT

A method for treating a medical pathology includes receiving a first set of acoustic radiation scattered by a volume of tissue containing at least a portion of the medical pathology and thereafter, changing a temperature of the volume of tissue. The method also includes thereafter, receiving a second set of acoustic radiation scattered by the volume of tissue and localizing the portion of the medical pathology from the first and second sets of received acoustic radiation. Localizing the portion of the medical pathology comprises identifying the medical pathology from differences in the first and second sets of received acoustic radiation resulting from the change in temperature. The method also includes insonifying the portion of the medical pathology with sufficient energy to damage the portion of the medical pathology.

54 Claims, 7 Drawing Sheets

U.S. PATENT DOCUMENTS

| | | | |
|---|---|---|---|
| 4,222,274 A | 9/1980 | Johnson | |
| 4,317,369 A | 3/1982 | Johnson | |
| 4,328,707 A | 5/1982 | Clement et al. | |
| 4,433,690 A | 2/1984 | Green et al. | |
| 4,509,368 A | 4/1985 | Whiting et al. | |
| 4,515,165 A | 5/1985 | Carroll | |
| 4,541,436 A | 9/1985 | Hassler et al. | |
| 4,542,744 A | 9/1985 | Barnes et al. | |
| 4,562,540 A | 12/1985 | Devaney | |
| 4,564,019 A | 1/1986 | Miwa | |
| 4,646,756 A * | 3/1987 | Watmough et al. | 607/154 |
| 4,662,222 A | 5/1987 | Johnson | |
| 4,671,256 A | 6/1987 | Lemelson | |
| 4,855,911 A | 8/1989 | Lele et al. | |
| 4,858,124 A | 8/1989 | Lizzi et al. | |
| 4,917,096 A | 4/1990 | Englehart et al. | |
| 4,941,474 A | 7/1990 | Pratt, Jr. | |
| 5,003,979 A | 4/1991 | Merickel et al. | |
| 5,029,476 A | 7/1991 | Metala | |
| RE33,672 E | 8/1991 | Miwa | |
| 5,095,909 A | 3/1992 | Nakayama et al. | |
| 5,143,069 A | 9/1992 | Kwon | |
| 5,158,071 A | 10/1992 | Umemura et al. | |
| 5,178,147 A | 1/1993 | Ophir et al. | |
| 5,179,455 A | 1/1993 | Garlick | |
| 5,212,571 A | 5/1993 | Garlick et al. | |
| 5,255,683 A | 10/1993 | Monaghan | |
| 5,260,871 A | 11/1993 | Goldberg | |
| 5,268,876 A | 12/1993 | Rachlin | |
| 5,269,309 A | 12/1993 | Fort et al. | |
| 5,280,788 A | 1/1994 | Janes et al. | |
| 5,304,173 A | 4/1994 | Kittrell et al. | |
| 5,305,752 A | 4/1994 | Spivey et al. | |
| 5,318,028 A | 6/1994 | Mitchell et al. | |
| 5,329,817 A | 7/1994 | Garlick et al. | |
| 5,339,282 A | 8/1994 | Kuhn et al. | |
| 5,349,954 A | 9/1994 | Tiemann et al. | |
| 5,413,108 A | 5/1995 | Alfano | |
| 5,415,164 A | 5/1995 | Faupel | |
| 5,433,202 A | 7/1995 | Mitchell et al. | |
| 5,463,548 A | 10/1995 | Asada et al. | |
| 5,465,722 A | 11/1995 | Fort et al. | |
| 5,474,072 A | 12/1995 | Shmulewitz | |
| 5,479,927 A | 1/1996 | Shmulewitz | |
| 5,485,839 A | 1/1996 | Aida et al. | |
| 5,487,387 A | 1/1996 | Trahey et al. | |
| 5,546,945 A | 8/1996 | Soldner | |
| 5,553,618 A | 9/1996 | Suzuki et al. | |
| 5,558,092 A | 9/1996 | Unger et al. | |
| 5,573,497 A | 11/1996 | Chapelon | |
| 5,582,173 A | 12/1996 | Li | |
| 5,588,032 A | 12/1996 | Johnson et al. | |
| 5,590,653 A | 1/1997 | Aida et al. | |
| 5,596,992 A | 1/1997 | Haaland et al. | |
| 5,606,971 A | 3/1997 | Sarvazyan | |
| 5,609,152 A | 3/1997 | Pellegrino et al. | |
| 5,620,479 A | 4/1997 | Diederich | |
| 5,640,956 A | 6/1997 | Getzinger et al. | |
| 5,643,179 A | 7/1997 | Fujimoto | |
| 5,664,573 A | 9/1997 | Shmulewitz | |
| 5,678,565 A | 10/1997 | Sarvazyan | |
| 5,722,411 A | 3/1998 | Suzuki et al. | |
| 5,743,863 A | 4/1998 | Chapelon | |
| 5,749,364 A * | 5/1998 | Sliwa et al. | 600/438 |
| 5,759,162 A | 6/1998 | Oppelt et al. | |
| 5,762,066 A | 6/1998 | Law et al. | |
| 5,766,129 A | 6/1998 | Mochizuki | |
| 5,797,849 A | 8/1998 | Vesely et al. | |
| 5,800,350 A | 9/1998 | Coppleson et al. | |
| 5,810,731 A | 9/1998 | Sarvazyan et al. | |
| 5,817,025 A | 10/1998 | Alekseev et al. | |
| 5,833,614 A | 11/1998 | Dodd et al. | |
| 5,846,202 A | 12/1998 | Ramamurthy et al. | |
| 5,855,554 A | 1/1999 | Schneider et al. | |
| 5,865,167 A | 2/1999 | Godik | |
| 5,865,743 A | 2/1999 | Godik | |
| 5,891,619 A | 4/1999 | Zakim et al. | |
| 6,002,958 A | 12/1999 | Godik | |
| 6,005,916 A | 12/1999 | Johnson et al. | |
| 6,023,632 A | 2/2000 | Wilk | |
| 6,050,943 A | 4/2000 | Slayton et al. | |
| 6,056,690 A | 5/2000 | Roberts | |
| 6,083,166 A | 7/2000 | Holdaway et al. | |
| 6,102,857 A | 8/2000 | Kruger | |
| 6,109,270 A | 8/2000 | Mah et al. | |
| 6,117,080 A | 9/2000 | Schwartz | |
| 6,135,960 A | 10/2000 | Holmberg | |
| 6,149,441 A | 11/2000 | Pellegrino | |
| 6,242,472 B1 * | 6/2001 | Sekins et al. | 514/396 |
| 6,289,235 B1 | 9/2001 | Webber et al. | |
| 6,292,682 B1 | 9/2001 | Kruger | |
| 6,296,489 B1 | 10/2001 | Blass et al. | |
| 6,317,617 B1 | 11/2001 | Gilhuijs et al. | |
| 6,368,275 B1 * | 4/2002 | Sliwa et al. | 600/437 |
| 6,385,474 B1 | 5/2002 | Rather et al. | |
| 6,413,219 B1 | 7/2002 | Avila et al. | |
| 6,450,960 B1 | 9/2002 | Rather et al. | |
| 6,475,150 B2 | 11/2002 | Haddad | |
| 6,478,739 B1 | 11/2002 | Hong | |
| 6,490,469 B2 * | 12/2002 | Candy | 600/407 |
| 6,511,427 B1 | 1/2003 | Sliwa, Jr. et al. | |
| 6,527,759 B1 * | 3/2003 | Tachibana et al. | 604/500 |
| 6,540,678 B2 | 4/2003 | Rather et al. | |
| 6,559,178 B1 * | 5/2003 | Zamoyski | 514/453 |
| 6,587,540 B1 | 7/2003 | Johnson et al. | |
| 6,636,584 B2 | 10/2003 | Johnson et al. | |
| 6,645,202 B1 * | 11/2003 | Pless et al. | 606/41 |
| 6,672,165 B2 | 1/2004 | Rather et al. | |
| 6,716,412 B2 * | 4/2004 | Unger | 424/9.52 |
| 6,728,567 B2 | 4/2004 | Rather et al. | |
| 6,776,760 B2 | 8/2004 | Marmarelis | |
| 6,785,570 B2 | 8/2004 | Nir | |
| 6,810,278 B2 | 10/2004 | Webber et al. | |
| 6,837,854 B2 | 1/2005 | Moore et al. | |
| 6,883,194 B2 | 4/2005 | Corbeil et al. | |
| 6,926,672 B2 | 8/2005 | Moore et al. | |
| 6,939,301 B2 | 9/2005 | Abdelhak | |
| 6,984,210 B2 | 1/2006 | Chambers et al. | |
| 7,025,725 B2 | 4/2006 | Dione et al. | |
| 7,179,449 B2 * | 2/2007 | Lanza et al. | 424/9.321 |
| 7,285,092 B2 | 10/2007 | Duric et al. | |
| 7,346,203 B2 | 3/2008 | Turek et al. | |
| 7,497,830 B2 | 3/2009 | Li | |
| 7,530,951 B2 | 5/2009 | Fehre et al. | |
| 7,556,602 B2 | 7/2009 | Wang et al. | |
| 7,570,742 B2 | 8/2009 | Johnson et al. | |
| 2001/0029334 A1 | 10/2001 | Graumann et al. | |
| 2001/0037075 A1 | 11/2001 | Candy et al. | |
| 2002/0065466 A1 | 5/2002 | Rather et al. | |
| 2002/0099290 A1 | 7/2002 | Haddad | |
| 2002/0131551 A1 | 9/2002 | Johnson | |
| 2003/0138053 A1 | 7/2003 | Candy | |
| 2004/0030227 A1 | 2/2004 | Littrup et al. | |
| 2004/0059265 A1 | 3/2004 | Candy et al. | |
| 2004/0167396 A1 | 8/2004 | Chambers et al. | |
| 2004/0181154 A1 | 9/2004 | Peterson et al. | |
| 2005/0260745 A1 | 11/2005 | Domansky et al. | |
| 2006/0009693 A1 | 1/2006 | Hanover et al. | |
| 2006/0020205 A1 | 1/2006 | Kamiyama | |
| 2006/0085049 A1 | 4/2006 | Cory et al. | |
| 2006/0287596 A1 | 12/2006 | Johnson et al. | |
| 2006/0293597 A1 | 12/2006 | Johnson et al. | |
| 2008/0045864 A1 | 2/2008 | Candy et al. | |
| 2008/0229832 A1 | 9/2008 | Huang et al. | |
| 2008/0275344 A1 | 11/2008 | Glide-Hurst et al. | |
| 2008/0294043 A1 | 11/2008 | Johnson et al. | |
| 2008/0319318 A1 | 12/2008 | Johnson et al. | |
| 2009/0035218 A1 | 2/2009 | Ross et al. | |

FOREIGN PATENT DOCUMENTS

| | | |
|---|---|---|
| EP | 0 351 610 A2 | 1/1990 |
| EP | 0 538 241 A2 | 4/1993 |
| EP | 0 538 241 B1 | 4/1993 |
| EP | 0 284 055 B1 | 9/1993 |
| EP | 0 609 922 A2 | 8/1994 |
| EP | 0 661 029 A1 | 7/1995 |
| EP | 0 774 276 A2 | 5/1997 |

| EP | 1063920 A | 1/2001 |
| --- | --- | --- |
| WO | 0228350 A | 4/2002 |
| WO | 0230288 A | 4/2002 |
| WO | WO 02/28350 A2 | 4/2002 |
| WO | 2005057467 A | 6/2005 |

OTHER PUBLICATIONS

Andre, et al: "A New Consideration of Diffraction Computed Tomography for Breast Imaging: Studies in Phantoms and Patients" *Acoustical Imaging*, J.P. Jones, Plenum Press,'NewYork (1995), • pp. 379-390.

Borup, et al. "Nonperiturbative Diffraction Tomography Via Gauss-Newton Iteration Applied to the Scattering Integral Equation" *Ultrasonic Imaging*, Academic Press, Inc. (1992) vol. 14, pp. 69-85.

Chelfouh, et al. "Characterization of Urinary Calculi: In Vitro of 'Twinkling Artifact' Revealed by Color-Flow Sonography" *American Journal of Roentgenology* (1998) vol. 171, pp. 1055-1060.

Dean, Stanley R., "The Radon Transform and Some of Its Applications" *Krieger Publishing Company*, Malabar, Florida (1993).

Gervias, et al. "Renal Cell Carcinoma: Clinical Experience and Technical Success with Radio-frequency Ablation of 42 Tumors[1]" *Radiology*, 2003, pp. 417-424, vol. 226.

Greenleaf, J.F. "Tissue Characterization with Ultrasound: vol. II: Results and Applications" *CRC Press, Inc.*, Boca Raton, Florida, pp. 95-122.

Greenleaf, J.F., et al. "Introduction to Computer Ultrasound Tomography" *Computed Aided Tomography and Ultrasonics in Medicine*, North-Holland. (1970); pp. 125-136.

Greenleaf, J.F., et al. "Mulitdimensional Visualization of Ultrasonic Images" *J. Acoust. Soc. Amer.* vol. 95 (2902), (1994).

Greenleaf, W.J. et al. "Artificial Cavitation Nuclei Significantly Enhance Acoustically Incuded Cell Transfection", *Ultrasound Med & Biol*, 1998, pp. 587-595, vol. 24.

Hebden, et al. "Acoustically Modulated Electrical Impedance Tomography" *Proceedings of the SPIE*, vol. 1231 (1990); pp. 7-14.

Jellins, J. "Breast Tissue Characterizations" *Tissue Characterization with Ultrasound*, vol. II, CRC Press, (1986); pp. 95-122.

Johnson, et al. "Modeling of Inverse Scattering and Other Tomographic Algorithms in Conjunction with Wide Bandwidth Acoustic Transducer Arrays for Towed or Autonomous Sub-bottom Imaging Systems" *Proceedings of Mastering the Oceans Through Technology*, Oceans Newport, Rhode Island, USA, (Oct. 26-29, 1992), pp. 294-299.

Johnson, et al. "Comparison of Inverse Scattering and Other Tomographic Imaging Algorithms Using Simulated and Tank Data for Modeling Subbottom Imaging Systems" IEEE Oceans '93 Symposium, Nov. 1993, vol. I, pp. 458-492 (1993).

Louvar, et al. "Correlation of Color Doppler Flow in the Prostate with Tissue Microvascularity" *Cancer*, (Jul. 1998) vol. 1:83 (1); pp. 135-140.

Miller, DL et al. "Sonoporation of Cultured Cells in the Rotating Tube Exposure System", *Ultrasound Med & Biol*, 1999, pp. 143-149, vol. 25.

Nelson, et al. "Interactive Acquisition, Analysis and Visualization of Sonographic Volume Data" *International Journal of Imaging Systems and Technology* (1997) vol. 8(26), pp. 26-37.

Noble, et al. "Spleen Hemostasis Using High-Intensity Ultrasound: Survival and Healing", *Journal of Trauma Injury, Infection, and Critical Care*, 2002, pp. 1115-1120, vol. 53, No. 6.

Sehgal, et al. "Visualization of Breast Calcification by Acoustic Resonance Imaging" *Radiology Supplement*, 84th Scientific Assembly and Annual Meeting, Nov. 29-Dec. 4, 1998 presented in McCormick Place, Chicago, Illinois (1998) vol. 209, listing: 1150.

Shi, et al: "Effects of Pressure Changes on Harmonic and Subharmonic Response of US Contrast Microbubbles" 84th Scientific Assembly and Annual Meeting, Nov. 29-Dec. 4, 1998 presented in McCormick Place, Chicago, Illinois (1998) vol. 209, listing: 1154.

Vaezy,S. et al. "Real-Time Visualization of High-Intensity Focused Ultrasound Treatment Using Ultrasound Imaging" *Ultrasound in Medicine & Biology*, 2001, pp. 33-42, vol. 27, No. 1.

Wiskin, et al. "Full Inverse Scattering vs. Born-like Approximation for Imaging in a Stratified Ocean" *Proc. of Engineering in harmony with the Ocean* (Oceans '93), Victoria, British Columbia, Oct. 1993.

Yankelevitz, et al. "Small Pulmonary Nodules: Volumetrically Determined Growth Rates Based on CT Evaluation" *Radiology*, Oct. 2000, pp. 251-256, vol. 217.

*Centerline*, PortalVision section, Summer 2002 edition, Published by Varian Medical Systems.

Diederich, C. J. et al., "The Design of Ultrasound Applicators for Interstitial Hyperthermia," 1993 Ultrasonics Symposium, IEEE, pp. 1215-1219, 1993.

Azhari et al., "Volumetric Imaging with Ultrasonic Spiral CT," Radiol 212 (1999) 270-275.

Barlow et al., "Prospective Breast Cancer Risk Prediction Model for Women Undergoing Screening Mammogrpahy," J. Nat'l Cancer Institute 98(17): 1204-1214 (2006).

Boone et al., "Dedicated Breast CT: Radiation Dose and Image Quality Evaluation," Med Phys 221(3): 657-667 (2001).

Boston et al., "Estimation of the Content of Fat and Parenchyma in Breast Tissue Using MRI T1 Histograms and Phantoms," MRI 23: 591-599 (2005).

Boyd, "Quantitative Classification of Mammographic Densities and Breast Cancer Risk: Results from the Canadian National Breast Screening Study," J Nat'l Cancer Institute 87(9): 670-675 (1995).

Byng et al., The Quantitative Analysis of Mammographic Densities,: Phys Med Biol 39 (1994) 1629-1638.

Chang et al., "Breast Density Analysis in 3-D Whole Breast Ultrasound Images," IEEE Proc 28th IEEE EMBS Annual International Conference (2006) 2795-2798.

Chen et al., "Projecting Absolute Invasive Breast Cancer Risk in White Women with a Model that Includes Mammographic Density," J. Nat'l Cancer Institute 98(17) (2006) 1215-1226.

Diederich et al., "The design of ultrasound applicators for interstitial hyperthermia," Ultrasonics Symposium, Proc IEEE 1993 Baltimore, MD, USA Oct. 31-Nov. 3, 1993, New York, NY, USA, 1215-1219.

Duric et al., "Detection of Breast Cancer with Ultrasound Tomography: First Results with the Computed Ultrasound Risk Evaluation (CURE) Prototype," Med Phys 34(2) (2007).

Dussik, "The Ultrasonic Field as a Medical Tool," Amer J Phys Med 33(1) (1954) 5-20.

Glide et al., "Novel Approach to Evaluating Breast Density Utilizing Ultrasound Tomography," Med Phys 34(2) (2007) 744-753.

Glide, "A Novel Approach to Evaluating Breast Density Using Ultrasound Tomography," Dissertation Graduate School of Wayne State University (2007).

Glide-Hurst et al., "A Novel Ultrasonic Method for Measuring Breast Density and Breast Cancer Risk," Med Imaging 2008, Proc SPIE vol. 6920, 69200Q.

Glide-Hurst, "A New Method for Quantitative Analysis of Mammographic Density," Med Phys 34(11) (2007) 4491-4498.

Greenleaf, "Computerized Tomography with Ultrasound," Proc IEEE 71(3) (1983) 330-337.

Hayashi, "A New Method of Measuring in Vivo Sound Speed in the Reflection Mode," J Clin Ultrasound 16(2) (1988) 87-93.

Jellins et al., "Velocity Compensation in Water-Coupled Breast Echography," Ultrasonics 11(5) (1973) 223-6.

Kaizer et al., "Ultrasonographically Defined Parenchymal Patternrs of the Breast: Relationship to Mammographic Patterns and Other Risk Factors for Breast Cancer," Brit J Radiology 61(722) (1988) 118-24.

Karssemeijer, "Automated Classification of Parenchymal Patterns in Mammograms," Phys Med Biol 43 (1998) 365-378.

Kerlikowske et al., "Longitudinal Measurement of Clinical Mammographic Breast Density to Improve Estimation of Breast Cancer Risk," J. Nat'l Cancer Institute 99(5) (2007) 386-395.

Kossoff et al., "Average Velocity of Ultrasound in the Human Female Breast," J Acoust Soc America 53(6) (1973) 1730-6.

Li et al., "Clinical Breast Imaging Using Sound-Speed Reconstructions of Ultrasound Tomography Data," Med Imaging 2008, Proc SPIE vol. 6920, 6920009.

Marias, "Automatic Labelling and BI-RADS Characterisation of Mammogram Densities," Proc 2005 IEEE, Sep. 1-4, 2005, pp. 6394-6398.

Mast, "Empirical Relationships Between Acoustic Parameters in Human Soft Tissues," Acoust Research Letters Online, Nov. 16, 2000, pp. 37-42.

Masugata et al., "Relationship Between Myocardial Tissue Density Measured by Microgravimetry and Sound Speed Measured by Acoustic Microscopy," Ultrasound in Med & Biol 25(9) (1999) 1459-1463.

Ophir et al., "Elastography: Ultrasonic Estimation and Imaging of the Elastic Properties of Tissues," Proc Instn Mech Engrs 213(Part H) (1999) 203-233.

Palomares et al., "Mammographic Density Correlation with Gail Model Breast Cancer Risk Estimates and Component Risk Factors," Cancer Epidemiol Biomarkers Prey 15(7) (2006) 1324-1330.

Robinson et al., "Quantitative Sonography," Ultrasound in Med & Biol 12(7): 555-65 (1986).

Teubner et al., "Comparative Studies of Various Echomammography," Ultraschall in Der Medizin 3(3) (1982) 109-18, G. Thieme Verlag, Stuttgart/New York.

Wei et al., "Correlation Between Mammographic Density and Volumetric Fibroglandular Tissue Estimated on Breast MR Images," Med Phys 31(4) (2004) 933-942.

Weiwad et al., "Direct Measurement of Sound Velocity in Various Specimens of Breast Tissue," Invest Radiol 35(12) (2000) 721-6.

Wolfe, "Risk for Breast Cancer Development Determined by Mammographic Parenchymal Pattern," Cancer 37(5) (1976) 2486-2493.

Yaffe, "Breast Cancer Risk and Measured Mammographic Density," Eur J Cancer Prevention 7(1) (1998) S47-55.

Palomares et al., "Mammographic Density Correlation with Gail Model Breast Cancer Risk Estimates and Component Risk Factors," Cancer Epidemiol Biomarkers Prev 15(7) (2006) 1324-1330.

* cited by examiner

| REF. NO. | ELEMENT |
|---|---|
| 102 | Sensor System |
| 104 | Data Acquisition and Control System |
| 106 | Reconstruction and Display System |

| REF. NO. | ELEMENT |
|---|---|
| 202 | Sensors |
| 206 | Switch |
| 208 | Single Board Computer |
| 210 | DAC |
| 212 | Power Amplifier |
| 214 | Filter |
| 216 | Signal Conditioner |
| 218 | Motion Control Subsystem |

*Fig. 2B*
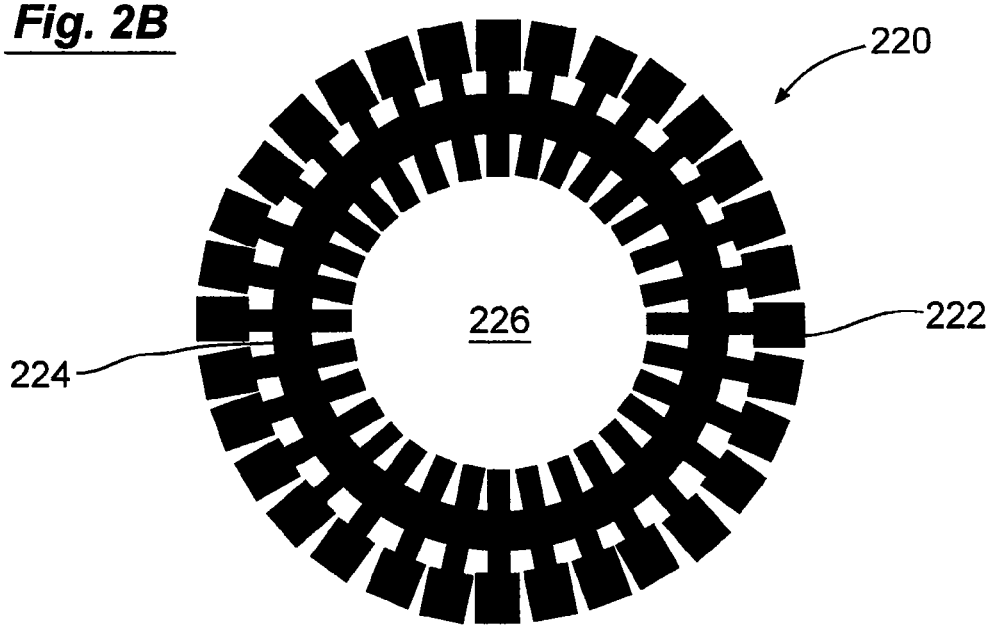
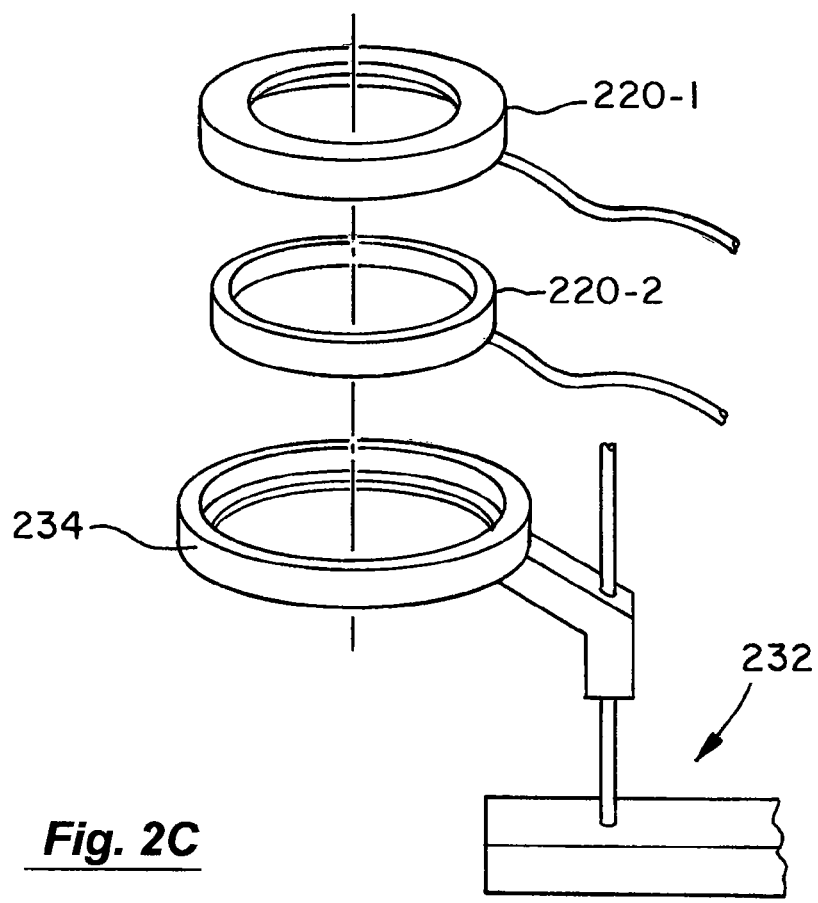
*Fig. 2C*

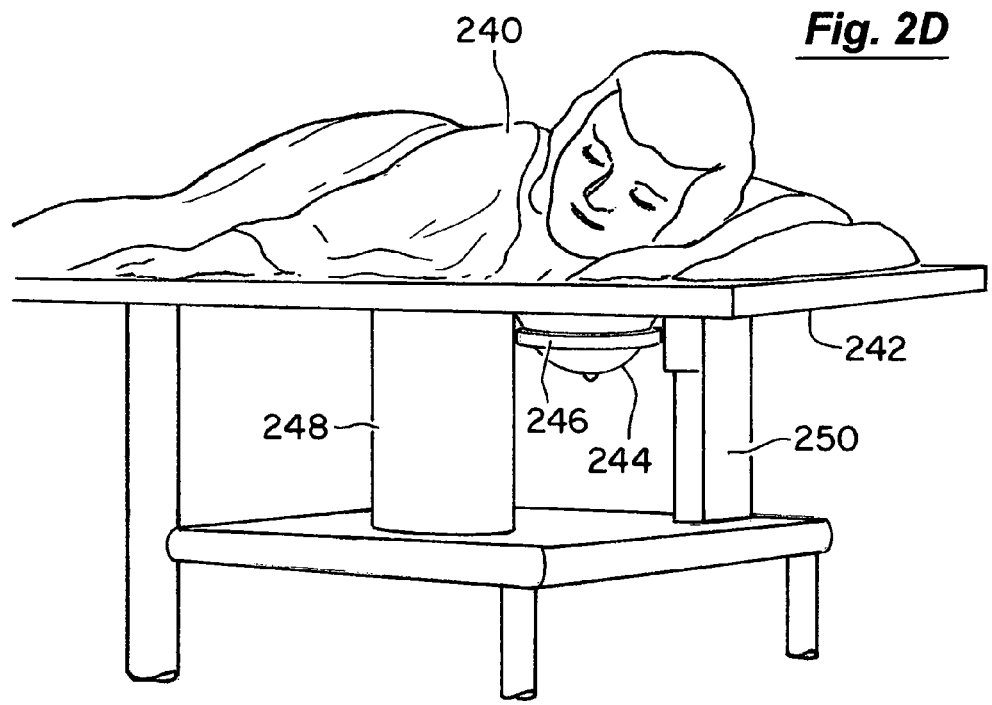
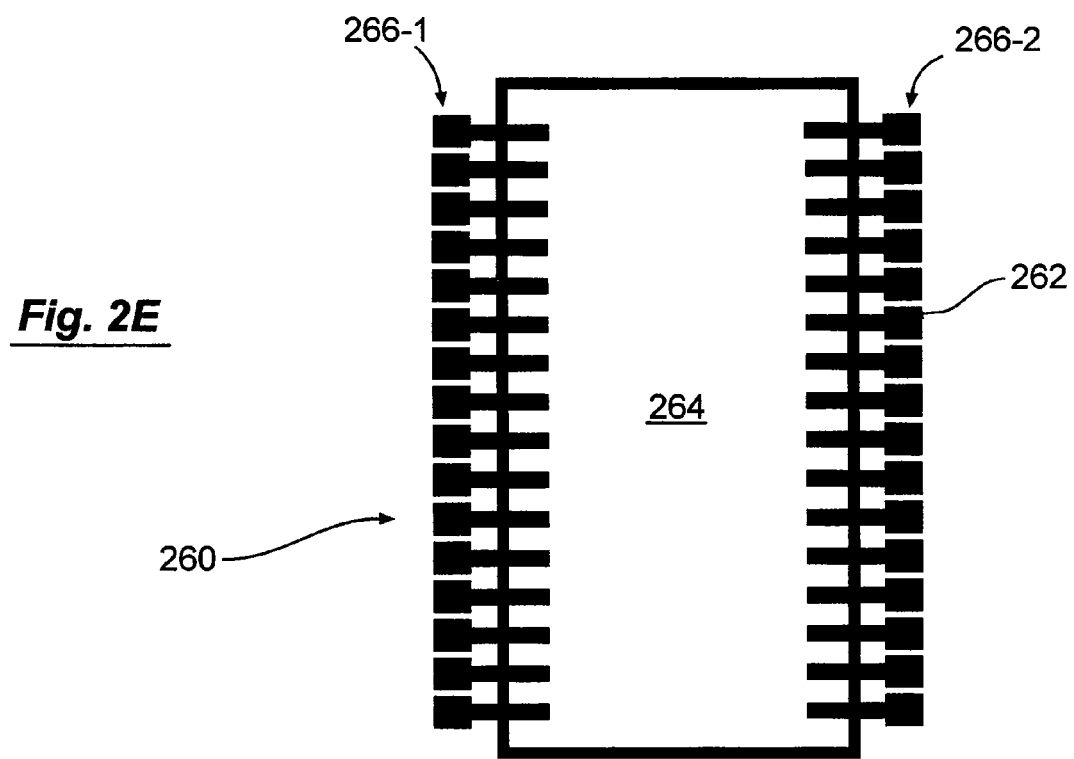

METHOD AND APPARATUS FOR COMBINED DIAGNOSTIC AND THERAPEUTIC ULTRASOUND SYSTEM INCORPORATING NONINVASIVE THERMOMETRY, ABLATION CONTROL AND AUTOMATION

CROSS-REFERENCES TO RELATED APPLICATIONS

This application is a non-provisional of and claims the benefit of U.S. Provisional Patent Application No. 60/381,022, filed on May 16, 2002 entitled METHOD AND APPARATUS FOR COMBINED DIAGNOSTIC AND THERAPEUTIC ULTRASOUND SYSTEM INCORPORATING NONINVASIVE THERMOMETRY, ABLATION CONTROL AND AUTOMATION, the entire disclosure of which is herein incorporated by reference for all purposes. This application is a continuation-in-part of and claims the benefit of U.S. patent application Ser. No. 10/323,467, filed on Dec. 18, 2002, entitled "DIAGNOSTIC ANALYSIS OF ULTRASOUND DATA," issued on Jan. 10, 2006 as U.S. Pat. No. 6,984,210, and is a continuation-in-part of and claims the benefit of U.S. patent application Ser. No. 10/323,354, filed on Dec. 18, 2002, entitled "COMPUTERIZED ULTRASOUND RISK EVALUATION SYSTEM," issued on Oct. 23, 2007 as U.S. Pat. No. 7,285,092, the entire disclosures of which are herein incorporated by reference for all purposes.

This application is related to commonly assigned U.S. patent application Ser. No. 09/994,025, filed Nov. 26, 2001, issued on Apr. 27, 2004 as U.S. Pat. No. 6,728,567, the entire disclosure of which is incorporated herein by reference in its entirety. This application also is related to U.S. patent application Ser. No. 09/809,961, entitled "DYNAMIC FOCUSING OF ULTRASOUND FOR MASS REMOVAL IN TISSUE," filed Mar. 14, 2001 by James V. Candy, issued on Dec. 3, 2002 as U.S. Pat. No. 6,490,469, which is a nonprovisional application of and claims the benefit of U.S. Provisional Patent Application No. 60/348,018, entitled "DYNAMIC ACOUSTIC FOCUSING FOR NONINVASIVE TREATMENT," filed Nov. 8, 2001 by James V. Candy, the entire disclosures of which are incorporated herein by reference for all purposes.

BACKGROUND OF THE INVENTION

The present invention relates generally to imaging systems. More particularly, the present invention relates to ultrasound imaging systems with therapeutic capabilities.

There are a number of disadvantages associated with various imaging systems that are currently in use, particularly when used for medical applications. For example, a number of imaging techniques, such as x-ray imaging, mammography, and computed tomographic (CT) scans, use ionizing radiation that presents a risk of cell mutation when used medically. Also, CT scans and magnetic resonance imaging (MRI) techniques both involve procedures that are relatively expensive, a factor that by itself acts to some degree to limit their use. A significant disadvantage of methods such as mammography is that they rely on two-dimensional images that may disguise three-dimensional structure information that can be critical for diagnosis.

As an alternative to these imaging technologies, the medical community has looked to ultrasound for providing a safe, low-cost, high-resolution imaging tool. Further, some have reported that ultrasound may be used in advantageous ways for therapeutic benefits. These benefits, however, have not been fully realized.

There is, therefore, a need for systems and methods that provide improved diagnosis and therapy using ultrasound.

BRIEF SUMMARY OF THE INVENTION

Embodiments of the invention thus provide a method of treating tissue comprising a medical pathology. The method includes receiving, in a first diagnostic session, acoustic signals scattered from the tissue with a plurality of acoustic detectors disposed to at least partially surround at least a portion of the tissue. The method also includes delivering, in a therapeutic session, therapy to the medical pathology, and thereafter, in a second diagnostic session, evaluating the effect of the therapy on the medical pathology by receiving acoustic signals scattered from the tissue with the plurality of acoustic detectors. The first and second diagnostic secessions are comprised by a single diagnostic/therapy session and occur substantially contemporaneously with each other. At least one of the diagnostic sessions may include deriving a temperature-related diagnostic parameter from the received acoustic signals.

In other embodiments, a method for treating a medical pathology includes receiving a first set of acoustic radiation scattered by a volume of tissue containing at least a portion of the medical pathology. The method also includes thereafter, changing a temperature of the volume of tissue, and thereafter, receiving a second set of acoustic radiation scattered by the volume of tissue. The method also includes localizing the portion of the medical pathology from the first and second sets of received acoustic radiation. Localizing the portion of the medical pathology may include identifying the medical pathology from differences in the first and second sets of received acoustic radiation resulting from the change in temperature. The method also includes insonifying the portion of the medical pathology with sufficient energy to damage the portion of the medical pathology. Insonifying the portion of the medical pathology may include focusing acoustic radiation onto the portion of the medical pathology. Focusing the acoustic radiation may include simulating propagation of a divergent acoustic wave from a source positioned at a location of the portion of the medical pathology, determining an intensity of the simulated divergent acoustic wave at locations of acoustic sources, and activating the acoustic sources to produce a corresponding acoustic wave convergent on the location of the portion of the medical pathology.

In still other embodiments, a system for treating a medical pathology includes a sensing system configured to receive acoustic radiation scattered by a volume of tissue containing at least a portion of the medical pathology. The sensing system may includes sensors adapted to be disposed to at least partially surround the tissue. The system also includes a transmitting system configured to direct acoustic radiation at the medical pathology. The transmitting system includes transmitters adapted to be disposed to at least partially surround the tissue. The system also includes means for changing the temperature of the tissue. The system also includes a processing system programmed to process information representative of the received acoustic radiation and generate an acoustic image of the tissue, simulate propagation of a divergent acoustic wave from a source positioned at a location of the portion of the medical pathology determine an intensity of the simulated divergent acoustic wave at locations of the transmitters, and activate the transmitters to produce a corresponding acoustic wave convergent on the location of the portion of the medical pathology. The processing system may be further programmed to localize the portion of the medical pathology from multiple sets of received acoustic radiation.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components.

FIG. 2B illustrates an example of a ring transducer array.

FIG. 2C illustrates an example of a ring transducer assembly.

FIG. 2D illustrates an example of a ring transducer in use.

FIG. 2E illustrates an example of a paddle transducer array.

DETAILED DESCRIPTION OF THE INVENTION

Introduction:

Embodiments of the invention are directed generally to methods and systems for examining an object under study, such as tissue. Further, embodiments of the invention are directed toward systems and methods that employ acoustic radiation, such as ultrasound, to both diagnose and treat medical pathologies. Such diagnosis and treatment may employ temperature-related parameters to enhance discrimination among various tissue types.

Figure 1:
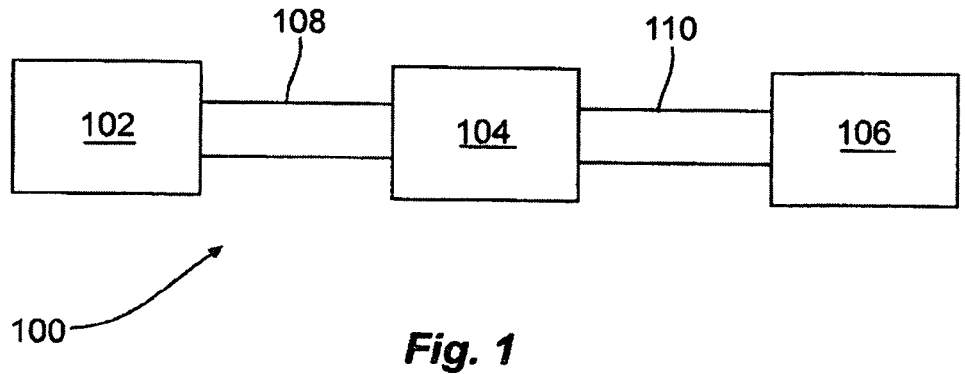
FIG. 1 illustrates a schematic diagram of an exemplary system according to embodiments of the invention.

System Overview:

Attention is directed to FIG. 1, which illustrates one embodiment of a system 100 according to the present invention. The system 100 includes a sensor system 102, a data acquisition and control system 104, and a reconstruction and display computer system 106, each of which will be described more fully hereinafter. The individual components are configured for communication via connections 108, 110, which may be electrical connections, optical connections, radio frequency (RF) connections, or the like, or any such combination. In a specific embodiment, connection 110 is an Ethernet connection. Previously-incorporated U.S. patent application Ser. No. 10/323,467 describes embodiments of similar systems in greater detail. Those skilled in the art will realize that the system 100 is exemplary and that other embodiments may be designed to operate according to the teachings of the present invention.

Figure 2A:
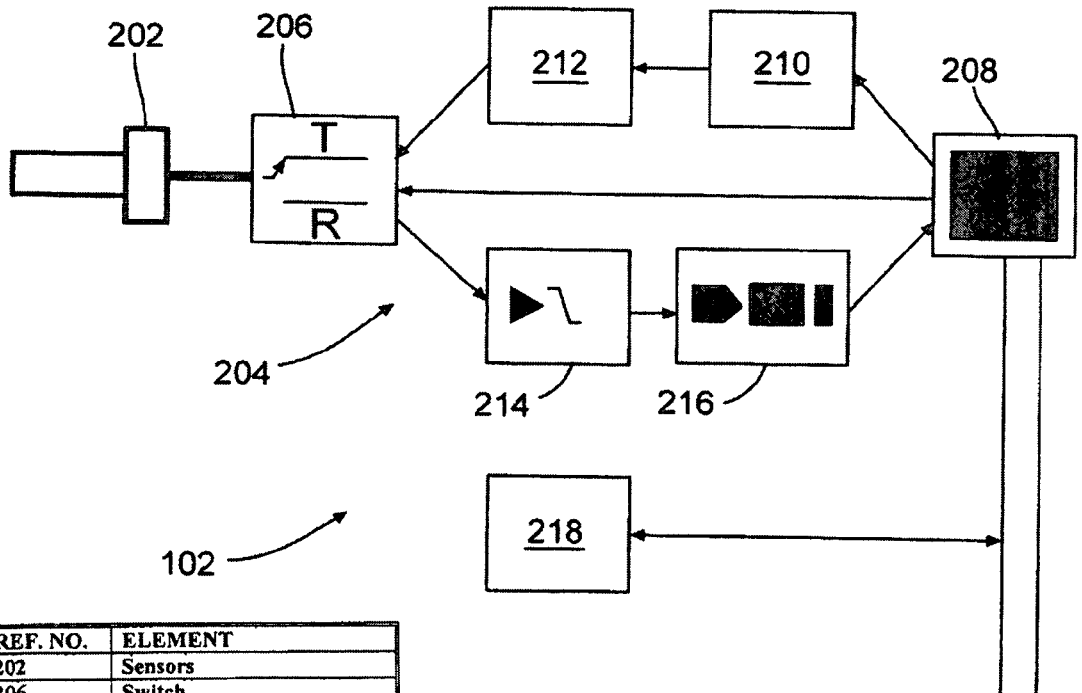
FIG. 2A illustrates a sensor system according to embodiments of the invention.

Sensor System:

The sensor system 102 may be any of a variety of embodiments that position transducers within sufficient proximity to tissue and thereby provide for the transmission and receipt of acoustic radiation. FIG. 2A illustrates the sensor system in greater detail.

The sensor system 102 includes a plurality of sensors 202, only one of which is illustrated in FIG. 2A for clarity. The sensors 202 typically are deployed in an array, as will be described. In some embodiments, the array is configured for movement with respect to tissue under study such that a plurality of 2-D data slices obtained from multiple perspectives may be reconstructed to form a 3-D image. Such systems are more fully described in previously-incorporated in U.S. patent application Ser. No. 10/323,467. In other embodiments, the sensor array is of sufficient size that the sensors may capture a number of 2-D slices without having to move the array with respect to the tissue.

Each sensor 202 is connected to the data acquisition system via interface electronics 204. The interface 204 includes a switch 206 that sets the sensor for either of a transmit or receive mode. The position of the switch is determined by a SBC 208 (Single Board Computer), or other appropriate computing device. In the transmit mode, the SBC receives a signal from the control system instructing that an ultrasonic pulse should be emitted. The SBC 208 initiates the pulse by sending a signal to a digital-to-analog converter 210 which shapes the pulse. The DAC 210 sends the signal to a power amplifier 212 that generates sufficient power for the pulse. The now-amplified signal travels through the switch 206, to the sensor 202, and into the tissue.

In a specific embodiment, a transmit system consists of digital waveform storage, digital-to-analog conversion, linear power amplification to drive the transducer elements, and a high voltage multiplexer to select the desired element(s). The transmit waveform is stored in memory internal to a FPGA (Field Programmable Gate Array). The waveform is clocked out to a DAC at a clock rate and timing as determined by the programming of the system, as set up by the prototype user. A linear power amplifier is used to provide the necessary element drive. High voltage multiplexer switches, such as the Supertex 20220 eight channel device, may steer the transmit signal to the desired element. The transmit system may be capable of generating diagnostic waveforms for electrical loopback testing and calibration of the analog transmit/receive (T/R) chain.

Returning to FIG. 2A, in the receive mode, the SBC sets the switch 206 accordingly. The sensor detects a signal, which is sent to a filter 214 via the switch 206. The filter 214 removes unwanted information, such as interference, and passes the useful information to a signal conditioner 216. The signal conditioner 216 may, among other things, convert an analog signal to a digital signal, process the signal to extract useful information from various frequency bands of the signal, and appropriately buffer the information for transmission to the data acquisition system. At the appropriate time, the information may be read out of a buffer by the SBC and transmitted to the data acquisition system.

In a specific embodiment, the receive signal conditioning path from the transducer element consists of a T/R switch, a low noise preamp, TGC (Time Gain Control) amplifier, anti-aliasing low pass filters, and an ADC. The T/R switch is a biased diode bridge which blocks large amplitude transmitted signals, but allows receive signals of amplitudes on the order of 1 volt or less to pass to the preamplifier. The low noise preamplifier and TGC amplifier are embodied in a number of commercial IC's. In this embodiment, a device such as the Analog Devices AD8332 may be used to support the required dynamic range. The TGC output stage drives anti-aliasing low-pass filters to a 12-bit ADC, such as the Analog Devices AD19235. The ADC data may be multiplexed in groups of four into the FPGA to allow reduced I/O port usage on the FPGA. The FPGA supports the higher data rates. This data may be written to standard PC133 SDRAM, or similar standard PC RAM to allow for economical data storage. Average writing rates of 40 MW/sec with 64-bit width supports 16 channels data streaming. Those skilled in the art will realize other embodiments of an electrical interface 500 that may perform the function of the present invention.

Returning to FIG. 2A, the sensor system 102 also includes, in some embodiments, a motion control subsystem 218. The motion control subsystem 218 receives power, and timing and control information from the data acquisition and control system 104, as will be described. The motion control system 218 moves the sensor array with respect to the tissue being examined.

As previously mentioned, the sensors 202 typically are arranged in an array. The array may be two-dimensional or three-dimensional. For example, a two-dimensional array may include 32 sensors arranged in a circular configuration or in an opposing "paddle" configuration, each of which will be described in greater detail. In other embodiments, the 32-sensor arrays may be duplicated in the third dimension to create a three-dimensional array. Other embodiments may include fewer or greater numbers of sensors and may be arranged in different configurations.

is adapted to receive a ring transducer acoustic array 220 as a modular insert. Thus, for example, an appropriately sized acoustic array 220 may be selected based on the size of the tissue to be examined so as to provide sufficient acoustic contact between the individual sensors comprised by the array and the tissue to be examined. A large acoustic array 220-1 and a small acoustic array 220-2 are illustrated. Other sizes of acoustic arrays may be used, which may be both smaller and larger than those illustrated. The mechanical system 230, including the acoustic array 220, may operate within a fluid bath, such as a water bath, as will be described.

The drive system 232 may be, for example, a threaded rod that transports the acoustic array 220 vertically with respect to the tissue to be examined. Other types of drive systems are possible and may be designed to transport the acoustic array 220 in different directions or combinations of directions. The drive system 232 allows the system to acquire a series of ultrasound 2-D slices that combine to make a 3-D data set.

Figure 4:
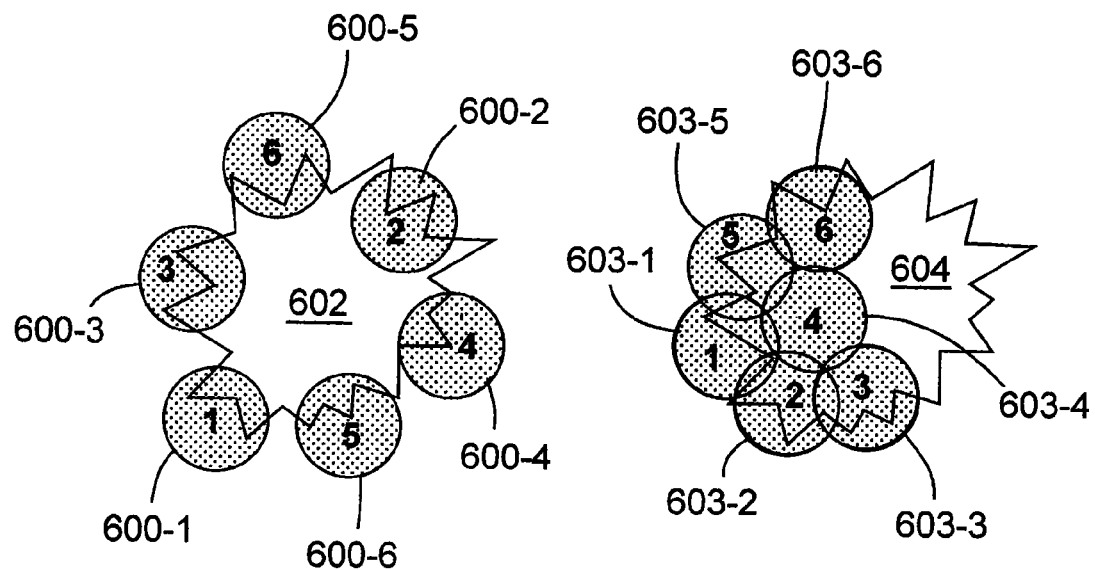
FIG. 4 illustrates two examples of staggered tissue ablation.

In a specific embodiment, the ring transducer may be designed according to the following specifications:

| | |
|---|---|
| Number of elements | 256 |
| Geometry | equally spaced on 15 cm diameter circle (1.84 mm pitch), or alternately, on linear segments of a 16-sided inscribed polygon. In either case, the actual positions of the transducer elements may be known within 0.2 mm within the imaging plane of the transducer. |
| Center frequency f0 | 2 MHz within ±5% average over all elements within ±10% for any individual element |
| Bandwidth | 60% f0 minimum, each element (−6 db transmit/receive) |
| Pulse ringdown (−20 db) | 1.8 us maximum |
| Element sensitivity variation over array | within 3 db band |
| Element angular response (at f0 in plane of circle) | −6 db max. at ±60 degrees |
| Element width (reference only) | 0.5 mm approx |
| Element elevation focus depth | 7.5 ± 1 cm |
| Elevation beam width at focus | 3 mm |
| Nominal element height (reference only) | 15 mm |
| Electrical interface | separate, identical cables for each 16 element sections |
| Mechanical interface | ring transducer elements/array sections mounted within a supporting ring structure. This ring structure will be secured in the ring support as illustrated in FIG. 4.4. |

Ring Transducer

In one embodiment the sensor system 102 is a ring transducer system. In another embodiment, the sensor system is a paddle transducer system. An embodiment of a ring transducer system is illustrated in FIG. 2B.

FIG. 2B illustrates a cross-sectional view of a ring transducer array 220. The ring transducer array 220 includes an array of individual sensors 222 and a supporting infrastructure 224. The sensors 222 surround, at least partially, an opening 226 in which tissue to be examined may be placed. Although illustrated as being circular, the ring transducer array 220 may have a multi-faceted polygonal shape, may be elliptical, or may even not be a closed figure in some embodiments.

As illustrated in FIG. 2C, the ring transducer array 220 may be mounted in a mechanical system 230 that provides, in some embodiments, motion via a software-controlled stepper motor system or other similar drive system 232. The mechanical system 230 includes an acoustic array support 234, which FIG. 2D illustrates one possible arrangement of an embodiment of the present invention using a ring transducer system. A patient 240 lies on an examining table 242. The tissue to be examined, in this case a breast 244, protrudes through a hole in the examining table. A ring transducer 246 surrounds the breast. A fluid bath 248 aid in acoustically coupling the transducer to the breast. During examination and/or treatment, a drive system 250 moves the transducer with respect to the breast.

In a specific embodiment, the drive system 250 provides electrical control of vertical motion, but is otherwise fixed within the fluid bath. In such embodiments, the transducer cabling may be routed over the upper edge of the water bath. The lead screw actuator for the vertical drive may be the sole fluid boundary penetration for this assembly. The motor drive for the assembly may be below the fluid bath. Electrical cables for limit switches, etc. located inside the fluid bath may also be routed over the upper edge of the bath.

Paddle Transducer

FIG. 2E illustrates a cross-sectional view of a paddle transducer array 260. Like the ring transducer array 220, the sensors 262 of the paddle transducer array 260 surround, at least partially, an opening 264 in which the tissue to be examined may be placed. The paddle transducer array 260 includes two individual paddles 266 that may be adjusted with respect to one another. The paddle transducer array 260 may have a different acoustic geometry than the ring transducer array 220, but may be designed to be electrically equivalent. That is, the paddles 266 of a paddle architecture may function with the same electronic subsystem as the ring transducer array 220.

In a specific embodiment, a paddle transducer system may be designed according to the following specifications:

| | |
|---|---|
| Center frequency f0 | 2 MHz within ±5% average over all elements within ±10% for any individual element |
| Bandwidth | 60% f0 minimum, each element (−6 db transmit/receive) |
| Pulse ringdown (−20 db) | 1.8 us maximum |
| Element sensitivity variation over array | within 3 db band |
| Element angular response (at f0 in plane of circle) | −6 db max. at ±60 degrees |
| Element width (reference only) | 0.5 mm approx |
| Element elevation focus depth | 7.5 ± 1 cm |
| Elevation beam width at focus | 1.5 mm |
| Nominal element height (reference only) | 15 mm |
| Electrical interface | separate, identical cables for each 16 element sections |
| Mechanical interface | paddle arrays constructed in a modular fashion to allow simple mounting in the paddle mechanical assembly, and to allow relatively simple change of transducer arrays with minimal or no change in the basic paddle mechanical structure and control mechanisms. |

Figure 2F:
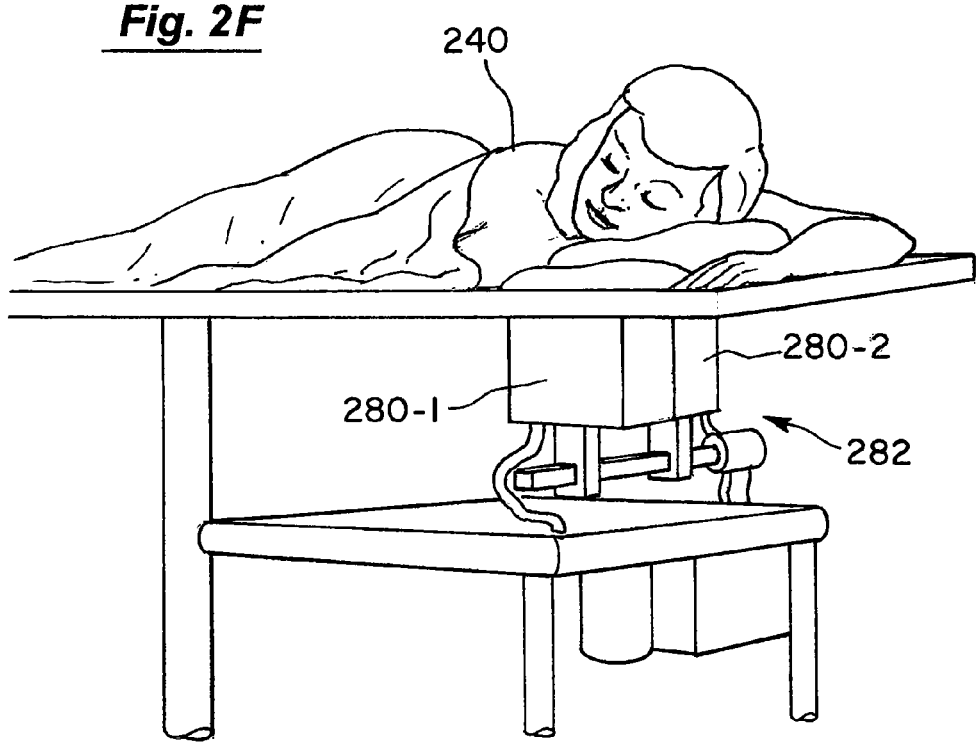
FIG. 2F illustrates an example of a paddle transducer in use.

FIG. 2F illustrates one possible arrangement of an embodiment of the present invention using a paddle transducer system. As with the arrangement described with respect to FIG. 2D, a patient's breast is examined. In this case, however, the breast is placed between two paddles 280 of the paddle transducer array 282. The paddles 280 may be adjusted to directly contact the tissue, thereby providing sufficient acoustic coupling to avoid the use of a fluid bath. This embodiment may, however, benefit from some type of medium (e.g., gel) to enhance the acoustic coupling. The paddle transducer system may be configured for movement with respect to the tissue to be examined or may be fixed. Embodiments of a paddle transducer system are described more fully in previously-incorporated U.S. patent application Ser. No. 10/323,467.

Figure 2G:
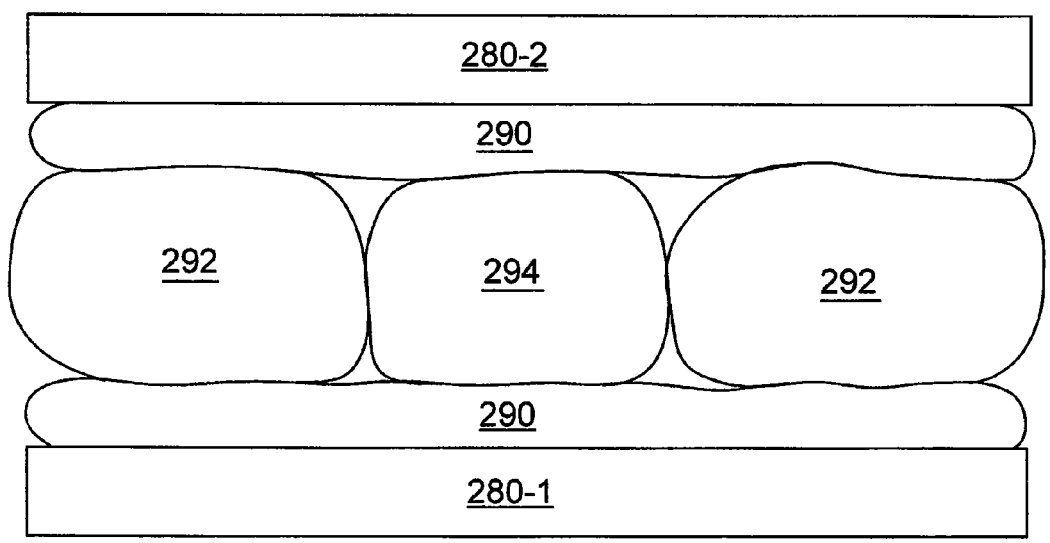
FIG. 2G illustrates an example of a paddle transducer system incorporating coupling bladders.

FIG. 2G illustrates an example of a paddle transducer system incorporating acoustically-coupling, pliable bladders. The bladders, which are filled with a medium that is acoustically matched to the transmission medium improve contact between the tissue under examination and the transducer array. In this example, lateral bladders 290 extend along the paddles 280, while removable bladders 292 are placed on either side of the tissue under examination 294. By filling the void that may otherwise exist between the paddles on either side of the tissue, less interference corrupts acoustic signals traversing these regions.

Figure 3:
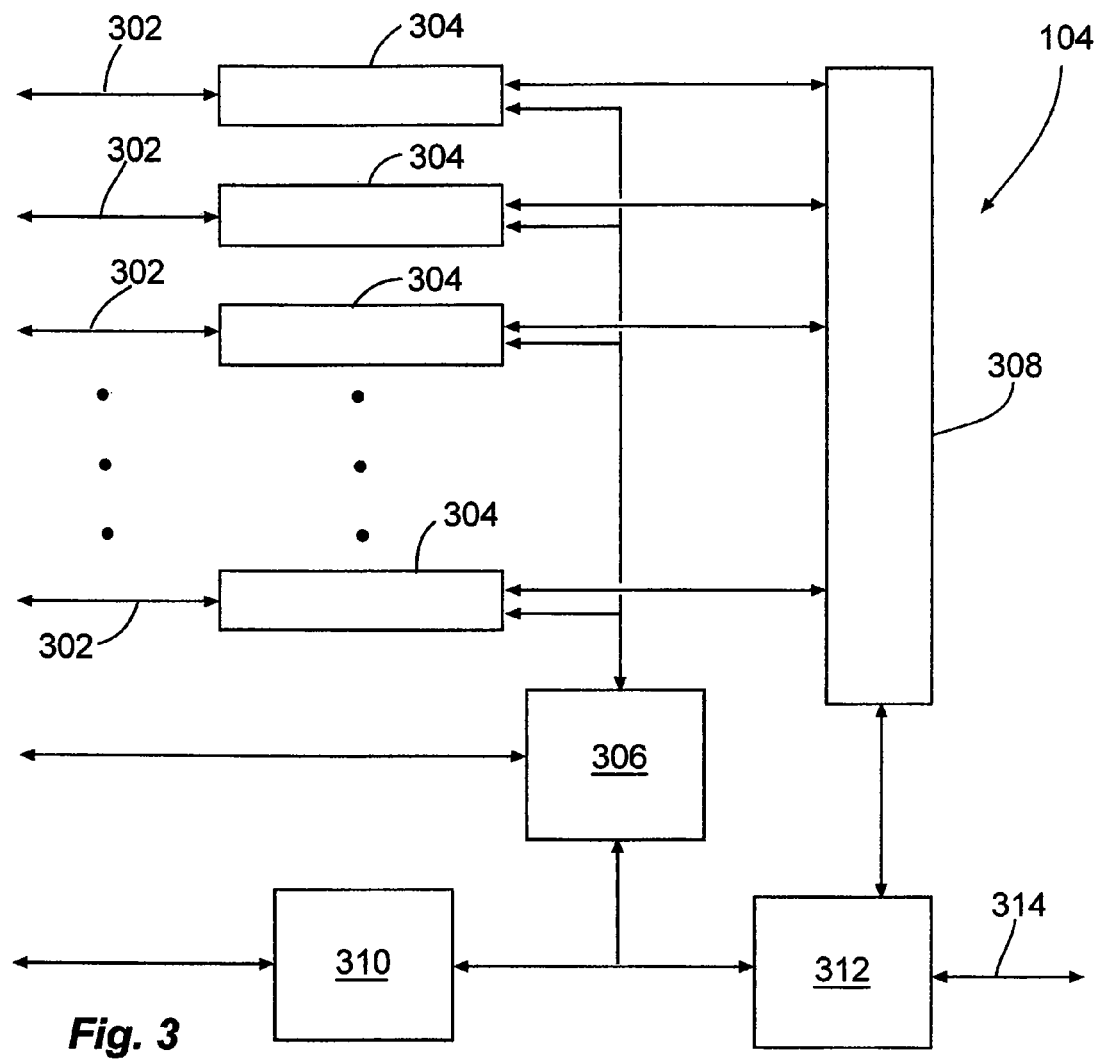
FIG. 3 illustrates a schematic diagram of a data acquisition and control system according to embodiments of the invention.

Data Acquisition and Control System:

FIG. 3 illustrates one exemplary embodiment of a data acquisition and control system 104 according to embodiments of the present invention. The data acquisition and control system 104 includes one or more interface connections 302 between individual sensors or groups of sensors in the sensor system 102 and channel boards 304. The channel boards 304 receive timing and control signals from a timing and control subsystem 306, as will be described, and thereby operate the sensors of the sensor system. The channel boards 304 are also interfaced to a backplane 308. The data acquisition and control system 104 also includes a power subsystem 310, and a computer subsystem 312.

Channel Board

Each channel board 304 provides for transmit excitation, signal conditioning, and data storage for one or more sensors. Each board may plug into an appropriately-configured backplane 308. Each board may function independently of other channel boards in the system.

In a specific embodiment, each board contains an FPGA which provides all of the real time control of timing, transmit, acquisition functions, and data memory interface. The FPGA firmware is stored in flash memory on the board, or downloaded from the Compact PCI computer. The FPGA generates all clocks and timing local to the channel board from the system clock and synchronization provided to each board.

Timing and Control Subsystem

The timing and control subsystem 306 provides basic clock and synchronization information among the multiplicity of independent channel board assemblies. The signals, programmed under control from the computer 312, are synchronized among all of the channel boards. The boards then each generate locally the timing, waveforms, and acquisition appropriate for the programmed acoustic line.

In addition to an internal programmed timing mode, the system may be capable of external triggering and gating. This capability allows for cardiac gated studies and single shot experiments as example uses of this mode.

Power Subsystem

The power subsystem 310 supports electronics and control for a minimum of 256 element transducers and associated support electronics in a specific embodiment. The power system may provide isolation to appropriate medical safety standards, especially in embodiments designed for human patients. The system may operate on standard 115VAC, 60 Hz nominal AC mains.

Computer System

In a specific embodiment, the back end may consist of a "standard" Intel-based computer board in compact PCI form factor. Such computer boards are available in configurations that support standard, commercial network and computer systems and software to allow networking with the reconstruction/display workstation.

In a specific embodiment, in order to maintain proper isolation independent of the commercial computer equipment, an optical Ethernet link 314 may connect the data acquisition and control system to the reconstruction and display computer system 106. This allows any commercial grade computer equipment to be used for this external computer system without compromising the integrity of the isolation to medical standards. Copper, optical, or other links may be used for any other network connections.

Data Acquisition and Control System Summary

In a specific embodiment, except for some peripheral control functions, the bulk of the data acquisition and control system 104 is contained in a Compact PCI chassis. Commercial mechanical chassis assemblies, backplanes and Intel-based computer boards are available in this standard, allowing the system to exist on a standard platform base. The transmit/receive (T/R) section of the electronic subsystem is divided into multiple, identical board assemblies with 16 channels receive channels and 1-8 transmit amplifiers. Since certain operating modes may have only one acoustic element transmitting at a time, there may be relatively few transmit amplifiers, which are multiplexed to the transducer elements with high voltage switches. Each channel board has its own transmit circuitry in order to avoid signal interconnections among the channel boards. Each board has an independent cable to its set of transducer acoustic elements. Except for clocks, timing synchronization, and power, each board assembly will function independently of other channel boards. Each of these boards has a PCI backplane interface to the Compact PCI computer board. Each channel provides a wide dynamic range acquisition system with real-time, RF data storage in RAM local to the channel board. Sufficient RAM memory is provided to store a study with a minimum of 100 2-D ultrasound slice data. Once stored, the data may be uploaded to the computer system without any real time restrictions. However, computational time requirements may constrain or dictate certain aspects of the computer system. In addition to changing the transducer, increasing the array size may be accommodated by adding additional channel boards, providing the clocks with timing and power, with the interfacing being supported within the compact PCI chassis.

Reconstruction and Display Computer System:

The reconstruction and display computer system 106 may comprise any of a variety of computing systems. For example, the reconstruction and display computer system may be the operator system described more fully in previously-incorporated U.S. patent application Ser. No. 10/323,467. Those skilled in the art will realize other alternative embodiments.

Having described a system according to embodiments of the present invention, applications to which the system may be applied will be described.

Method Overview:

The diagnostic component of the present invention extends the capabilities of a variety of other devices and techniques, to include temperature-related diagnostic parameters with treatment delivery, monitoring, interactive control and/or automation. Such robust ultrasound ("US") algorithms and recent imaging achievements with fewer transducer pairs (i.e., sparse array) has allowed for: 1) additional transducers in the array for higher powered US energy delivery/monitoring; or 2) simply utilizing the diagnostic array to also deliver sufficient cumulative US energy.

The ability to perform temperature-related cancer discrimination, treatment monitoring and ablation confirmation in a single apparatus represents a platform technology that can easily be applied to many treatment applications. Embodiments of the present invention extend known diagnostic parameters of ultrasonic fields (i.e., reflectivity, sound speed, attenuation, etc.) to include differential tissue responses to heating and/or cooling of tissue (i.e., additional cancer discrimination from benign tissue). For example, accurate temperature measurements during treatment (e.g., conversion of sound speed) confirms tumor ablation margins and also allows accurate fat-suppression imaging to reduce imaging time and data storage. Thermal treatment planning is possible through continuous monitoring of tissue response to thermal ablation (i.e., heat ablation>50° C., or cryotherapy<−20° C., or associated recovery from cooling/heating). Rapid imaging (<1 sec.) during treatment thus provides additional characterization of cancer margins during treatment (i.e., temperature changes in US parameters). In addition, the permanent changes in several thermodynamic and acoustic parameters provide confirmation of thorough treatment effect while the patient is still on the table, as well as for subsequent follow-up. Beyond high temperature ablation, several other uses are within the scope of the invention. Current hyperthermia (i.e., 41-44° C.) treatment systems could be used in combination with radiation therapy to avoid invasive thermometry. In alternative embodiments, advanced diagnostic functions with focused ultrasound target the delivery of chemotherapy, or genetic, agents contained in microbubbles "tuned" to burst at appropriate US energy and/or tumor locations.

"Dynamic focusing" in terms of a method and apparatus for generating destructive US energy by transmitting a time-reversed field to their original scattering point within a medium (e.g., tissue) is described more fully in previously-incorporated U.S. Patent No. 6,490,469. Diagnostic parameters according to embodiments of the present invention may be used to improve dynamic focusing-based thermal therapy as described in more detail herein.

By including temperature-related information, the apparatus described above has the capability of performing any or all of the following:

A. Directly measure the parameters of the acoustic field using a system according to the present invention.

B. Markedly reduce scan times and data storage by "fat-suppression" imaging. Static, or temperature-related dynamic, changes in US parameters first identify fatty tissues, then tailor subsequent cancer discrimination sequences to separation of benign and malignant responses.

C. Monitor temperature changes in all areas of the imaging field to <1° C. via thermoacoustic properties of the ultrasound field during heating and cooling cycles of an ablation modality (i.e., all heating sources, as well as cryotherapy, or freezing).

D. Deliver focused US energy to any region of a specified target (i.e., tumor area) and measure resultant changes in dynamic__ acoustic parameters in order to:
  1. Provide further differentiation of tumor from normal tissue by their heating or cooling responses.
  2. Monitor target temperature for automatic downregulation/itermination of ablation, (heating or cooling) to that region
  3. Treatment protocol development: Selectively stop heating in one location and begin in another according to temperature or anatomy, thus allowing selective ablation of:

a. Tumor vascularity (i.e., "feeder" vessels) to decrease convective cooling of flowing blood and improve intratumoral heating profile.
b. All tumor contours for uniform ablation
c. Peripheral viable tumor while avoiding regions of central tumor necrosis not requiring intensive treatment.
d. Regions needing immediate re-treatment due to tumor heterogeneity and/or ineffective initial heating cycle.

E. Post-ablation: re-assess final acoustic parameters to confirm thorough coagulation necrosis and any residual tumor viability over time F. Ensure greater safety and reduced treatment times using Dynamic Focusing since thermal build-up from cumulative exposure is avoided (i.e., multiple transducer focusing rather than using a single emitter).

MRI Temperature Monitoring and High-Intensity Focused Ultrasound

The technique of high intensity focused ultrasound ("HIFU") has been extensively documented for multiple treatments and organ sites and is well known to those of skill in the art. The feasibility of impressive treatment planning according to embodiments of the present invention has been demonstrated by the extensive work done with MRI thermal dosimetry. MRI temperature monitoring has reached clinical testing but may suffer broad application and acceptance due to its complexity, cost, and extended treatment times. The noted difficulties may therefore make MRI guidance "a long run for a short slide." However, the scientific analyses of temperature monitoring gives the system according to embodiments of the present invention a more direct path to human application since temperature-based treatment protocols have been developed for a clinical device for breast HIFU. MRI-guided HIFU treatment protocols have been limited to fibroadenoma trials in the United States, but have extended to breast cancer in Europe. Both of these trials required treatment times of 1-2 hours for each patient, depending upon tumor sizes of only 1-2 cm. Despite optimizing treatment delays between each US pulse, treatment times needed to be this long to avoid thermal build-up near the transducer from cumulative US exposure at a single delivery site.

When sonication pulses are delivered too close together in time or spacing, the additive temperature may cause unevenly shaped, larger lesions that can eventually cause tissue boiling. The resultant gas bubbles then scatter and reflect the subsequent US pulses, depositing the US energy in front of the bubbles and even closer to the transducer. An irregular lesion shape also suggests that the treatment was not delivered to the intended target area and could damage intervening tissues. Patient safety and sufficient US energy delivery to the target for adequate treatment therefore mandated interpulse delays, resulting in long patient treatment times. Even then, only 6 of 11 fibroadenomas showed complete ablation according to some sources. One patient developed a bruise following therapy due to unavoidable air bubble migration from the injection site of the local anesthetic beneath the fibroadenoma to the tissues in front of the mass and between the transducer. Similar to the air bubbles from cooked tissue, US energy deposition occurred away from the tumor and closer to the skin. It was also noted that adjacent fat caused some temperature hot spots to be invisible since the proton-resonant shift frequency of the MRI imaging sequence is not temperature-sensitive in fat. In fact, only 48% of sonications ($^{172}/_{356}$) were visualized and minor patient motion during the long procedure caused most of the temperature inaccuracies. Hope was noted for future fat-suppression and faster imaging techniques.

Ignoring the impractical, long treatment times for MRI-guided HIFU, the experience with generating MRI temperature-related dosimetry substantiates its utility and feasibility. Embodiments of the present invention that generate an US-based thermal dosimetry system in a single device for improved safety and reduced treatment times are well founded. Namely, three methods have been used to predict tissue damage:
 a.) power output and exposure length
 b.) critical temperature, and
 c.) entire temperature history to estimate thermal dose.

Temperature and dosimetry (i.e., b & c above) are independent of inhomogeneities of acoustic properties, but recent power calculations have allowed reasonable estimates despite power prediction differences between tissue types. Thermal dose shows good correlation with standard hyperthermia treatments for planned outcomes of 100% necrosis (i.e., 43° C. when delivered for 240 minutes). Conversion to predict HIFU outcomes yielded the following boundary criteria for unaffected (i.e., reversible) and thoroughly ablated tissue:

No tissue changes: <4.3 minutes at 43° C., with temperatures <47° C.

Complete tissue necrosis: >31.2 minutes at 43° C., with temperatures >50.4° C.

Using these practical guidelines, embodiments of the present invention not only use the temperature and dose profiles but have improved power estimates due to thorough knowledge of the US field. Embodiments of the invention include MRI-based thermal dosimetry for treatment planning in connection with US imaging and/or therapy.

Thermoacoustic Computed Tomography

Evidence is emerging for expanded cancer diagnostics using the differential tumor response to heating, substantiating the new temperature-related monitoring capabilities of the system according to embodiments of the present invention. Another breast imaging technology under development, thermoacoustic computed tomography (TCT), specifically relies upon the greater heating response of tumors over benign tissue. Since breast tumors appear to have a higher bound-water fraction than benign tissue (i.e., 0.85 vs. 0.75, resp.), tissue heating by pulsed radio-frequency (RF) energy would be greater, and/or faster, for tumors. Only ~0.25° C. tissue heating caused mechanical expansion of tissue that initiated pressure waves. The waves propagated through the tissue as sound and were detected by US transducers. Differential waves from breast cancer were shown in vivo, but the images were much worse than in vitro images of a pig kidney. Their in vivo technical difficulties were listed as poor RF penetration of deep tissue (i.e., at 434 MHz), motion and skin interface artifacts. However, the poor detail of other anatomic structures in their breast images also suggest that their reconstruction algorithms had insufficient resolution in highly scattering breast tissue. They acknowledged the need to integrate TCT with more sophisticated ultrasound according to at least one report, but failed to show high anatomic detail of other breast tissues. Despite their technical problems, they have effectively validated that differential tumor response to heating has been observed.

Elastography—MRI and US

In simple terms, as a steak cooks its texture changes from soft to firm. Once cooked, its firmness is permanent. Diagnostics according to embodiments of the present invention similarly define the irreversible "firmness" in regions of heat ablation by their acoustic properties. Elastography has demonstrated excellent delineation of final HIFU lesions in liver. However, their ex vivo technique using direct tissue compression has less clinical promise than less invasive vibrational techniques. One example of a diagnostic parameter was shear modulus since cancers have lower vibrational amplitude than softer adjacent tissues. Recently, vibrational elastography for tissue mapping has been validated using phase-contrast-based magnetic resonance imaging (MRI) techniques. An article (Kruger R A, Kiser W L and SpantzT. Thermoacoustic CT of the breast. Medical Imaging 2002: Physics of Medical Imaging (SPIE 2002). Paper 4682-55. San Diego, Calif., herein incorporated by reference in its entirety) thoroughly documents the relationships between shear modulus, acoustic strain wave frequency, resolution, phase changes and temperature. It has thus been identified that the premise of elastographic tumor discrimination may additionally include effects from temperature-related changes. Elastography thus serves as an excellent post-ablation assessment of irreversible tissue damage that will complement other US parameters (below). As imaging speed of vibrational sequences improves, dynamic elastography will provide additional on-line evaluation during treatments.

US Temperature Monitoring Parameters

The determination of acoustic properties for temperature monitoring have been addressed by heating curves of sound speed vs. temperature, while delineation of the final ablation area has also been quantified and imaged. The heating curves showed that sound speed increased as temperature increased for all tissue types, except fat. For temperatures between ~32-36° C., fat had a negative sound speed response to heating due to a phase change related to melting of some fat components (i.e., sound speed in more liquefied fat<solid fat). Sound speed for fat also has been verified as significantly slower than all other breast tissues. However, other breast tissues had significant overlap in sound speed measurements for these fresh excised specimens. The previously noted separate heating curves for each tissue type thus appears discordant with the apparent insignificant difference in heating response of benign and malignant tissue. However, an interesting phenomenon in the heating curves (not specifically described) was the apparent differences in relative rate of change in sound speed vs. temperature changes for each tissue. Namely, the following table was derived from available data ranges of previous reports.

TABLE I

| Tissue | Temp (° C.) | $m \cdot sec^{-1} \cdot °C.^{-1}$ |
|---|---|---|
| Water | 24–36 | 2.7 |
| 0.9% NaCl | 24–40 | 1.8 |
| Liver | 24–36 | 1.3 |
| Breast parenchyma | 24–36 | 1.3 |
| Breast fat | 32–36 | −10.0 |
| Breast fat | 36–43 | 4.5 |
| Glycerol | 20–30 | −2.2 |
| Breast fat | 30–37 | −6.0 |
| Multiple myeloma | 22–37 | 1.3 |

These studies demonstrate that while nearly all tissues and fluid show increasing sound speed as temperature increases, they may do so in a unique manner for each tissue. While sound speed has shown clear separation of fat from glandular tissue, the unique heating profile of fat allows further separation based on heating response (i.e., even at temperatures >36° C., fat ~4.5 $m \cdot sec^{-1} \cdot °C.^{-1}$ vs. only 1.3 $m \cdot sec^{-1} \cdot °C.^{-1}$ for breast parenchyma). Embodiments of the present invention thus use a technique that may be characterized as "fat-suppression" breast imaging. Advanced diagnostic parameters of embodiments of the present invention then focus only on the non-fatty tissues, thereby reducing scanning times and data storage. Fluids also appear to have a different heating response than solid tissues, but the heating response of human breast cysts may relate to their lipid or serous content (i.e., 'oil' vs. 'simple' breast cysts).

While the multiple myeloma tumor had similar heating response as breast (i.e., 1.3 $m \cdot sec^{-1} \cdot °C.^{-1}$), the non-linear aspect (i.e., B/A) of the heating response was different for liver and multiple myeloma tumor, despite their similar sound speeds. The value of B/A is thus related to other thermodynamic parameters (i.e., Grusneissen parameters, Rao and Wade's constants), making it possible to obtain further characterization of the quasicrystalline structure (morphology) of tissues and their cohesive forces. A consequence of large-aperture diagnostic capabilities according to embodiments of the present invention is that differential tumor response to heating is greatly enhanced (i.e., $m \cdot sec^{-1} \cdot °C.^{-1}$, B/A, or other thermodynamic parameters). These new insights about tumor characterization complement the concepts of tumor morphology, margins and adjacent tissue reactions, or architectural distortion.

Final HIFU ablation areas have been characterized by permanent, marked increases in attenuation. To a lesser degree, sound speed still showed significant increases over pretreatment values. Final lesion attenuation and sound speed may thus be used to complement elastography and USAE to define irreversible tissue damage.

US-Stimulated Acoustic Emission (USAE) Thermometry: A Single Device

Embodiments of the invention provide for ultrasound-stimulated vibro-acoustic spectrography using diagnostic parameters of the ultrasound field. In addition, these teachings may be used to detect breast microcalcifications and for temperature monitoring and characterization of HIFU ablation regions. These joint concepts are integrated into the system described above with the previously-described hydrophone-type sensor(s) in the transducer array. USAE applies a harmonic excitation inside a target through the application of two focused beams that oscillate at slightly different frequencies. The US fields only overlap at the target, causing it to locally vibrate at the beat frequency. The response recorded at the hydrophone then depends on the local acoustic and mechanical properties of the target tissue. Tissue properties of stiffness and absorption influence the magnitude of the USAE and are used to detect coagulation. One report demonstrates the dual function of focused ultrasound transducers as an USAE interrogation source, both during and after ablation. The 50-msec imaging pulse was interspersed between the focused US pulses and allowed intermittent monitoring of ablations in progress.

USAE amplitude measurements suggested that the transition to irreversible tissue damage at the point of coagulation corresponded with ~55° C., when muscle tissue typically coagulates. The near-linear correlation of USAE amplitude with temperature was also lost at 55° C. and correlates with tissue stiffness, marked changes in absorption and shear modulus. However, at least one source also noted an interesting departure from the coagulation theory for fat, which continued to have USAE correlation beyond coagulation temperatures. This again suggests a differential heating curve for fat, whereby a phase change, or "melting," occurred, producing a more "liquid" response above muscle coagulation temperatures (i.e., >55° C.) (Note also that a cooked steak shows "reversed" stiffness for fat, which becomes "softer," or liquefies, compared to its cooler uncooked state). Again, fat-suppression imaging according to embodiments of the present invention mitigates or avoids the USAE irregularities caused by adjacent fat.

An interesting correlate of sound speed heating/cooling parameier ($m \cdot sec^{-1\circ} C^{-1}$) according to embodiments of the present invention was seen in the differential USAE cooling rate between fat and muscle. Fat had a faster USAE cooling rate than muscle (i.e., 0.0146/° C. vs. 0.0086/° C., respectively) despite more similar heating rates (i.e., 0.0147/1° C. for fat vs. 0.0118/1° C. for muscle). Conversely, they made the point than muscle had different heating and cooling rates while fat appeared to heat and cool at the same rate. These factors again confirm the temperature-related cancer diagnostics used with embodiments of the present invention. Not only do tumors have a significantly different heating rate, which is exploited for thermoacoustic CT imaging, but the multiple diagnostic parameters according to embodiments of the present invention can effectively monitor differential cooling rates as well.

Sonoporation, or the "opening" of cell membranes, in response to low amplitude ultrasound can be either permanent or temporary. Permanent damage to the cell membrane results in eventual cell lysis, whereas temporary damage often causes the membrane "holes" to "re-seal". It has been noted that be temporary damage, or reparable sonoporation, takes place in the presence of injected microbubbles at acoustic pressure amplitudes of 0.1-0.12 MPa for 1 and 2.25 MHz, respectively. While contrast agents are becoming standard practice in other countries, none are currently Food and Drug Administration (FDA) approved within the United States. Therefore, if reparable sonoporation even occurs with current diagnostic ultrasound levels, new focusing possibilities for delivering targeted treatments may help justify their use. While current diagnostic ultrasound may cause some degree of sonoporation that can be histochemically detected, the lack of focusing to any tissue target, using a single diagnostic and therapeutic device, limits practicality of this observation. For example, microbubble delivery of chemo/genetic treatment agents to a tumor within the liver couldn't be limited to just the tumor since the diagnostic ultrasound energy would burst the bubbles in all portions of the liver visualized by the diagnostic ultrasound beam. According to embodiments of the present invention, devices having smaller numbers of transducers operating at ~1.5 MHz provide combined imaging and targeted sonoporation.

For sonoporation, appropriate software drives the electronics to simultaneously fire a variable number of ultrasound emitters (e.g., 10-300 emitters). In light of the teachings herein, those skilled in the art can envision other embodiments in which any number of emitters could be added to the ring, or rewiring of the current transducer boards to allow dual function of the transducers to both send and receive. Again, the sequenced emitting of ultrasound pulses becomes a function of software control, utilizing the model-based focusing technique.

For ablative purposes, additional transducers may need to be added to the imaging array in order to generate higher initial acoustic power than those used for diagnosis. Therefore, these additional transducers would need to be spaced throughout the array configurations appropriate for that body part. These may require separate wiring schemas to connect them to the main unit, but they can still be driven by software modifications of the above noted process for using model-based focusing algorithms. Regardless of the transducer configuration (e.g., circular array, or opposing paddle geometry), it is conceivable that any body part containing a tumor could be effectively addressed by sonoporation and/or ablative energy treatments according to embodiments of the present invention.

In order to maintain three-dimensional location accuracy, an interleaved scanning technique could easily be implemented for either sonoporation or ablative energy treatments. Similar scanning techniques have already been described with focused ultrasound using MRI guidance for ablation of breast fibroadenomas and cancer. The purpose of interleaved techniques allow imaging-treatment-imaging sequences to result in localization-treatment-monitoring, respectively. By combining imaging and treatment into one device, the delivery of interlaced sequences would become a function of the speed and accuracy of the equipment. In this manner, treatments will be administered at the rate of imaging localization, preventing inadvertent treatment due to patient motion within the time sequence to verify localization. In other words, the estimated 40 millisecond scan time for propagation and reception of an ultrasound pulse may then be followed by a treatment pulse from multiple transducers (diagnostic or therapeutic energies), resulting in immediate focusing to the selected target within a similar 40 millisecond return time.

Computer processing also allows a subsequent monitoring pulse to be quickly fired after the initial image and treatment pulse. Within ~150 milliseconds (i.e., 40+40+40+ . . . ), extremely fast processing could produce images of the target and treatment outcome. Image reconstruction times could be markedly reduced by limiting visualization to the target region (e.g., 1-10 cc), focusing assistance needs ("seeds", needle/US emitter discussed hereinafter) and margin auto-detection algorithms. Such millisecond accuracy in the delivery of subsequent pulses would not only help alleviate inadvertent patient motion, but also unavoidable motion from cardiac or respiratory changes. Similarly, any distortions of the ultrasound field from the initial treatment pulse (i.e., changes in monitored ultrasound parameters of sound speed, attenuation, reflectivity, etc.) could be compensated for in the subsequent treatment pulse. The software control therefore may rely upon the computer workstation to switch between algorithms which serve a diagnostic function and those which trigger the focused ultrasound sequences. Intermittent non-invasive temperature monitoring could thus use an intermittent data set processed by the sound speed algorithm, where as a margin-based assessment for anatomic treatment accuracy would intermittently employ a reflective algorithm (i.e., migration or full aperture tomography). As ablation nears completion, other algorithms can help determine the need for additional focused ultrasound ablations by assessment of elastography, attenuation, USAE, etc. The ability to rapidly switch between these data sets makes online ablation monitoring entirely feasible, similar to current MRI guidance and monitoring.

The previously described mechanism of assisted focused ultrasound delivery (i.e., pretreatment deposition of tumor marking "seeds", or a needle intimating a localizing ultrasound pulse) thus comes into expanded application. The algorithm for "blind" focusing upon a dominant scatterer (or known location of the internal ultrasound emitter within a needle tip) could be much faster than a model-based algorithm requiring several iterations to achieve accurate spatial localization. As previously noted, time-reversal ultrasound focusing can be simplified and markedly expedited by allowing ablations to proceed around a dominant reflector within the ultrasound field. Similar to current deposition of radiopaque markers within the prostate to help guide "on-line" external beam radiation therapy treatment of prostate cancer, a highly reflective ultrasound "seed" could be placed within the tumor prior to the focused ultrasound treatment session. Alternatively, an ultrasound emitting needle could be placed within the tumor immediately prior to initiation of the focused ultrasound treatment session. In this manner, the previously described interleaved imaging-treatment-imaging sequences could be markedly accelerated in terms of data image process requirements for delivery of the subsequent treatment pulses.

Embodiments of the present invention include a treatment planning workstation. Software currently exists for accurate 3-D volumetric assessments of tumor margins overtime. This type of exquisite margin analysis would be an example of the first step in creating a tailored pulse sequence to cover the entire tumor volume. The next step would be similar to radiation therapy planning software which tries to minimize side effects of the radiation in adjacent normal structures as it is delivered through predetermined "portals". Namely, multiple repeating US pulse sequences using the previously described image-treat alternating pattern would be distributed across the tumor volume to cover all visible margins. Depending upon adjacent critical structures, treatment would generally include up to 1 cm beyond the tumor to achieve "surgical margins". The size of each treatment zone during a single pulse sequence could be altered as needed for either their low power or high-power treatment options. For example, with reference to FIG. 4, a high-power ablation may choose to stagger each successive pulse 600-1, 600-2, 600-3, 600-4 . . . (in turn) in an opposing fashion across the tumor volume 602 in order to avoid heat-induced alterations in the sound propagation profiles (e.g., air bubbles from cavitation). Conversely, it may be appropriate for a sequential, wavefront-type propagation of adjacent treatment sites 603-1, 603-1, 603-3, 604-4 . . . (in turn) to proceed-across the entire targeted tissue volume 604.

The accuracy in delivering these ablation zones again relates to the interleaved imaging-treatment pulse sequences which may be predetermined from a treatment "planning scan". The 3-D spatial accuracy derives from matching the preoperative study with the obtained interleaved images using the following suggested guidance options:
 a.) the tumor landmark boundaries;
 b.) an internal reference reflector, or "seed";
 c.) an echo emitting localization needle.

The flexibility of choosing different treatment patterns, sizes and delivery rates opens several options for combination with current therapies as well.

Figure 5:
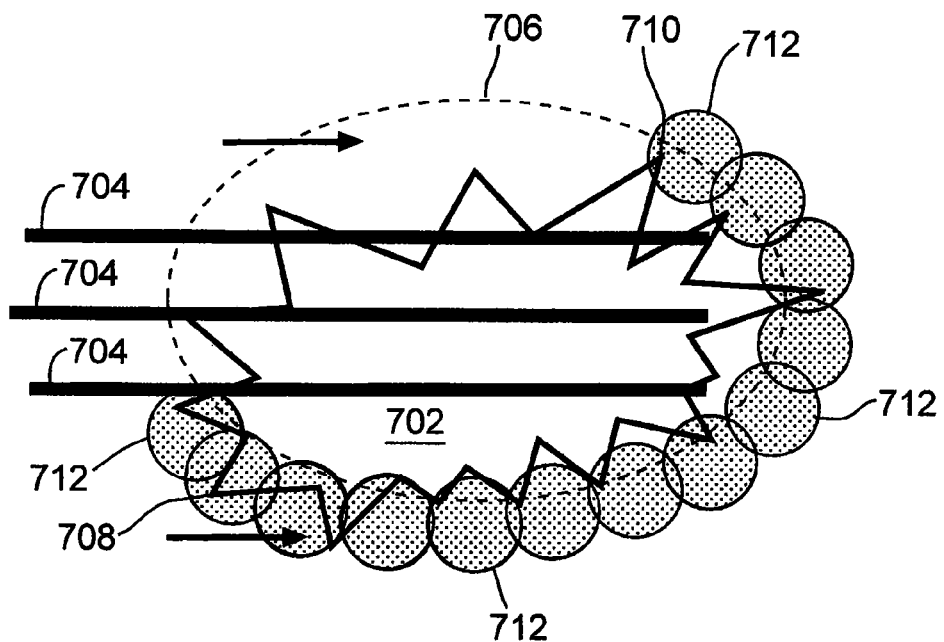
FIG. 5 illustrates an example of focused US-based tissue ablation combined with other therapies.

The above noted treatment patterns assume relatively large focal spot sizes compared to the overall tumor volume, such that the overall treatment times can be clinically limited (e.g., less.than 1 hour). Current HIFU experience suggests a relatiey time-consuming process (i. e., >2 hours for a 2 cm diameter fibroadenoma), whereby many small ablations were required to cover the larger volume. However, if only small treatment spot sizes are feasible [or in certain cases: different tissues and/or large tumor sizes (I >5 cm)], focused ultrasound may also serve an adjunctive role in combination with modalities capable of faster, large ablation volume. As seen in Fig. 5, a larger tumor 702 may, have the majority of its volume rapidly covered by percutaneous, ablation probes 704 placed strategically within the mass. However, these probe placements require technical accuracy that may be difficult to achieve, or the ablation 706 could become altered by adjacent heat sink effect from bordering vessels, such that portions of the tumor 702 may be left untreated. These untreated tumor margins 708, or those coming very close to the treatment margin 710, may be easily recognized using the previously noted temperature monitoring functions (e.g., sound speed) and parameters which evaluate ablation completeness (e.g. attenuation, USAE, elastography, etc.). Therefore, the smaller ablations 712 by focused ultrasound are shown to cover these untreated areas in the same therapy session. Alternatively, the "positive margins", known to occur with current ablations, could be treated at a later time by focused US according to embodiments of the present invention.

The use of additional ablation devices along with the proposed combined imaging and focused ultrasound device also raises the possibility of their control via the proposed monitoring and automation aspects used for the focused ultrasound device itself. Both cryotherapy and RF probes have thermocouples contained within their tips-but lack a-non-invasive mechanism to control the extent of their ablation. Current cryotherapy systems-use invasive thermocouples placed around the prostate to allow automated control of the cryotherapy probes within the prostate to "sculpt" the ice to the precise contours of the prostate, thereby limiting peripheral damage while maximizing cytotoxic efficacy. Therefore, the proposed imaging sequences could be used to monitor temperature and ablation thoroughness of both cryotherapy and heat-based; ablation systems. The focused ultrasound component could be used to not only "touch-up" incomplete margins as seen in FIG. 5, but also to prevent the inadvertent extension of cytotoxic ice formation by standard cryotherapy probes. This would lead to tailored "sculpting" of an ice ball in order to better conform to the contours of any delicate adjacent structures. For heat-based ablations, this degree of counteractive modulation of the major ablation zone may not be possible, but the major ablation can be terminated when one of its ablation margins reaches its targeted extent. Any remaining tumor ram could then be handled by the "touch-up" methodology seen in FIG. 5.

Whether the computer workstation uses interleaved scanning sequences with focused ultrasound as a stand-alone modality, or in combination with other ablative modalities noted above, the computer electronics required to control the switching between the algorithms are predominantly software driven. Driving of the transducers, data collection, storage and manipulation can be rapidly switched for their appropriate function.

Finally, the exquisite image localization, treatment application and monitoring described above for malignant tumor therapies can have broad applications to many other conditions and circumstances. Benign tumors could just as easily undergo the above noted imaging-treatment processes. Similarly, control of hemorrhaging from trauma would be markedly assisted by a single imaging and therapeutic device. Currently, hemorrhage control using a focused US device is quite limited by the relatively poor resolution, and subsequent localization, by standard reflection US and a large focused US array which could not only localize the point source of bleeding with fine detail of associated anatomic structures. As seen from images in other reports, visualization of a deeper hemorrhage is severely limited by penetration difficulties within the abdomen, resulting in severely degraded resolution. According to embodiments of the present invention, however, operating at, for example, 1.5 MHz, markedly improves resolution with deep penetration resulting in more accurate detection of hemorrhage and associated control from targeted ablation/hemostasis. In addition, rapid focusing by time-reversal techniques can also be markedly accelerated by using "blind" focusing to the brightest reflector within the visible field. In this case, a Doppler signal showing the actively escaping blood from the vessel could be brightest focused in the field.

Figure 6:
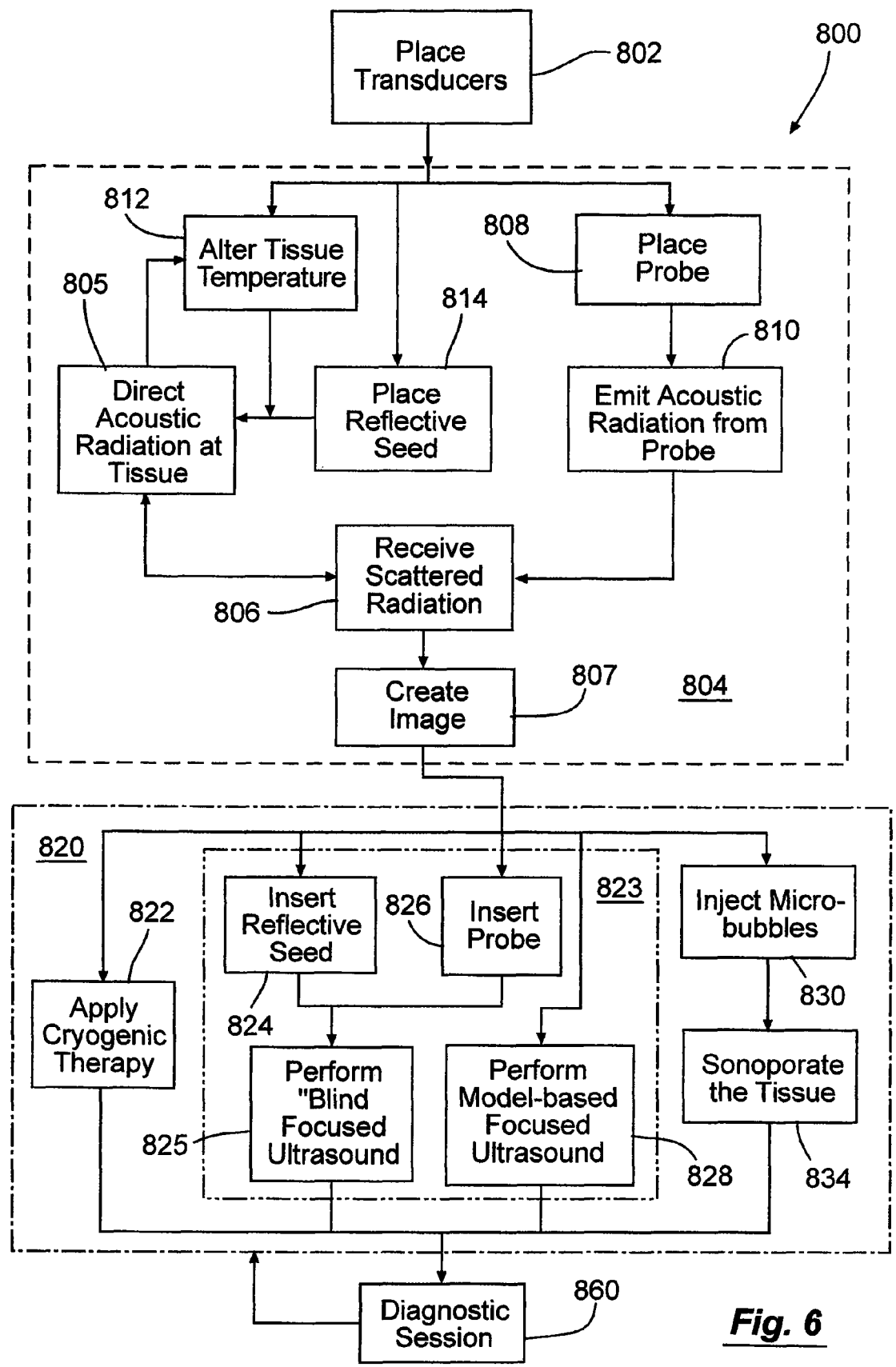
FIG. 6 illustrates a method according to embodiments of the present invention.

Accordingly, FIG. 6 illustrates a method 800 according embodiments of the present invention. The method may be implemented in the system of FIG. 1 or similar system. Those skilled in the art will realize that other embodiments of a method according to the present invention exist. Thus, the method of FIG. 6 is to be considered exemplary.

At block 802, a transducer array is positioned in relation to tissue to be examined. The transducer array may be a ring transducer, paddle transducers or other suitable transducer array. Further, the transducer array may be a 1-dimensional transducer array, a 2-dimensional transducer array, or a 3-dimensional transducer array. In this embodiment, the transducer array is configured to both transmit and receive acoustic radiation. Thus, the system is configured for both diagnosis and therapy. In some examples, the transducer array has a small number of transducers, for example, 11. In other examples, the simultaneous addressable emitter arrays both have a large number of transducers, for example several thousand. In some embodiments, the transmitters both transmit and receive. Many other examples are possible and not necessarily bounded by these two examples.

At block 804, acoustic imaging is performed. In some embodiments, acoustic radiation is directed at the tissue from transducers in the transducer array (block 805) and the resulting scattered radiation is received by other transducers in the array (block 806). In this way, an image of the tissue is obtained (block 807). In other embodiments, an acoustic radiation generating probe, for example an interstitial needle, is placed in the tissue (block 808) and acoustic radiation may be emitted from (block 810). The scattered radiation is then received at the transducers to form an image. In either of these cases, the image is, for example, a 3-dimensional image formed by compiling multiple 2-dimensional images. The image may be enhanced in any of the previously-described ways. For example, the temperature of the tissue may be either internally or externally altered to change the acoustic properties of the tissue (block 812). In such cases, a sound speed algorithm may be employed to further discriminate among various tissue types based on this acoustic property. The image also may be enhanced by placing a highly reflective "seed" into a particular area of the tissue of interest (block 814), for example a tumor, prior to directing the acoustic radiation at the tissue.

At block 820, therapy is performed on at least a portion of the tissue. The therapy may be any of a variety of different types of therapy, some of which were discussed herein previously. For example, a tumor located in the tissue may be treated with cryogenic (block 822) or ablative (block 823) therapies. The ablative therapy may involve the focusing of US acoustic radiation on a region of the tissue using time-reversal techniques as was described previously. Time-reversal focusing techniques may involve model-based focusing and/or "blind" focusing, both of which were described in more detail above.

In the case of blind focusing (block 825), the process may employ the use of natural body landmarks, such as bone, to direct the acoustic radiation. Blind focusing also may employ a reflective "seed" deposited within the target region (block 824). In other examples, interstitial needles, or other probes, are used which may: emit US radiation, measure temperature, and/or provide therapy, such as cryogenic therapy, radio frequency therapy, microwave therapy, or the like (block 826). Many other examples are possible.

In the case of model-based focusing (block 828), a person, such as a physician, may assist in defining the target region by supplying information to the diagnosis/treatment device. In some examples, the target region may be defined with the assistance of software. In some cases, these two examples are combined. In either of these examples, information developed from the operation at block 804 may be used. In still other examples, targeting information is supplied to the device from other sources. In yet other examples, the target is defined with respect to other objects at a known location in the tissue, again possibly employing information developed during the operation at block 804. Combinations of these examples also are possible as are many other examples.

In still other examples, the therapy provided at block 820 may involve sonoporation (block 830). This may involve low power focused US and/or high-re power focused US. This treatment may be combined with microbubbles, as previously described, to deliver chemical treatment to sonoporated cells (block 834).

In still other examples, the therapy may involve any combination of the foregoing. For example, a tissue area may be treated with cryogenic therapy while regions around the cryogenically-treated area are treated with focused US. Many other such examples are possible.

The therapy provided at block 820 may be directed toward are area of active hemorrhage. This may involve directing focused US using any of the previously-described techniques or may employ Doppler-based blind focusing. Other examples are possible.

The therapy provided at block 820 may be followed by a subsequent diagnostic session that uses US to determine the effect of the therapy. This may take place at block 860, as shown and may include any of the diagnostic processes described above with respect to block 804. In some examples, the operations of blocks 820 and 860 may be repeated any number of times to incrementally treat the tissue by iteratively treating the tissue then assessing the effect of the treatment. Many other examples are possible.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A method of treating tissue comprising a medical pathology, the method comprising:
   in a first diagnostic session, using a plurality of acoustic sensors to receive acoustic signals propagated through the tissue;
   in a first therapeutic session, applying time reversal focusing, based on the received acoustic signals, to deliver acoustic radiation therapy to the medical pathology; and
   in a subsequent diagnostic/therapeutic sequence, interleaving subsequent diagnostic sessions and subsequent therapy sessions to thereby treat a tumor volume comprised by the tissue;
   wherein each subsequent diagnostic session comprises receiving acoustic signals propagated through the tissue and each subsequent therapy session comprises applying time reversal focusing, based on the received acoustic signals, to deliver acoustic radiation therapy to the medical pathology; and
   wherein interleaving subsequent diagnostic sessions and subsequent therapy sessions comprises repeating the interleaving until a temperature-related diagnostic parameter derived from the received acoustic signals reaches a particular threshold.

2. The method of claim 1, wherein at least one of the diagnostic sessions comprises deriving an attenuation-related diagnostic parameter from the received acoustic signals.

3. The method of claim 1, wherein at least one of the diagnostic sessions comprises deriving an elastography-related diagnostic parameter from the received acoustic signals.

4. The method of claim 1, wherein the tissue is comprised by a patient and the subsequent diagnostic/therapeutic sequence comprises substantially no repositioning of the patient.

5. The method of claim 4, wherein the tissue is comprised by a portion of the patient selected from the group consisting of breast, brain, bone, liver, kidney, prostate, muscle, any soft tissue tumor, and blood vessel.

6. The method of claim 1, wherein applying time reversal focusing, based on the received acoustic signals, to deliver acoustic radiation therapy to the medical pathology comprises determining a focal point with an object proximate the tissue.

7. The method of claim 6, wherein the object is a natural object of a body comprising the tissue.

8. The method of claim 6, further comprising depositing an acoustically reflective seed into the tissue, wherein the object comprises the acoustically reflective seed.

9. The method of claim 1, wherein applying time reversal focusing, based on the received acoustic signals, to deliver acoustic radiation therapy to the medical pathology comprises placing an interstitial needle in the tissue.

10. The method of claim 9, further comprising emitting acoustic radiation from the interstitial needle.

11. The method of claim 9, further comprising measuring a parameter of the tissue with the interstitial needle.

12. The method of claim 11, wherein measuring a parameter of the tissue with the interstitial needle comprises measuring the temperature of the tissue.

13. The method of claim 9, further comprising delivering therapy to the tissue using the interstitial needle.

14. The method of claim 13, wherein the therapy comprises a selection from the group consisting of cryogenic therapy, heat-based therapy, laser therapy, radio frequency therapy, and microwave therapy.

15. The method of claim 13, wherein the therapy comprises cryogenic therapy in combination with acoustic radiation and the acoustic radiation is used to contour a region of the tissue to which the cryogenic therapy is delivered.

16. The method of claim 1, wherein applying time reversal focusing, based on the received acoustic signals, to deliver acoustic radiation therapy to the medical pathology comprises receiving information from a practitioner who at least partially defines a target region.

17. The method of claim 1, wherein applying time reversal focusing, based on the received acoustic signals, to deliver acoustic radiation therapy to the medical pathology comprises using software-based auto-detection to at least partially define a target region.

18. The method of claim 1, wherein applying time reversal focusing, based on the received acoustic signals, to deliver acoustic radiation therapy to the medical pathology comprises sonoporating at least a portion of the tissue.

19. The method of claim 1, wherein a subsequent therapy session comprises a different type of therapy than that applied in an immediately previous therapy session.

20. A method for treating a medical pathology, the method comprising:
placing an array of transducers comprising acoustic sources positioned to transmit acoustic radiation into tissue containing the medical pathology and acoustic receptors positioned to receive corresponding acoustic signals propagated through the tissue;
using the transducers to receive a first set of acoustic signals transmitted through the tissue;
changing a temperature of the tissue;
receiving a second set of acoustic signals transmitted through the tissue;
localizing the medical pathology from the first and second sets of received acoustic signals, wherein localizing the medical pathology comprises identifying the medical pathology from differences in the first and second sets of received acoustic signals resulting from the change in temperature, and wherein the differences in the first and second sets of received acoustic signals result from changes in the speed of sound through the volume of tissue; and
thereafter, insonifying the medical pathology with sufficient energy to damage the medical pathology by focusing acoustic radiation onto the portion of the medical pathology;
wherein focusing acoustic radiation comprises:
simulating propagation of divergent acoustic waves from a source positioned at the medical pathology;
determining an intensity of the simulated divergent acoustic waves at the acoustic sources; and
activating the acoustic sources to produce corresponding acoustic waves convergent at medical pathology.

21. The method recited in claim 20, wherein insonifying the medical pathology further comprises sonoporating the medical pathology.

22. The method recited in claim 21 further comprising delivering chemotherapy to the medical pathology substantially contemporaneously with insonifying the medical pathology.

23. The method recited in claim 22 wherein:
delivering chemotherapy to the medical pathology comprises delivering microbubbles containing the chemotherapy to the medical pathology; and
insonifying the medical pathology damages the microbubbles to release the chemotherapy.

24. The method recited in claim 21 further comprising delivering a genetic agent to the medical pathology substantially contemporaneously with insonifying the medical pathology.

25. The method recited in claim 24 wherein:
delivering the genetic agent to the medical pathology comprises delivering microbubbles containing the genetic agent to the medical pathology; and
insonifying the medical pathology damages the microbubbles to release the genetic agent.

26. The method recited in claim 20 wherein localizing the medical pathology further comprises identifying a three-dimensional boundary for the medical pathology.

27. The method recited in claim 20 wherein localizing the medical pathology further comprises correlating a known position of an acoustically reflective object proximate the medical pathology with a relative position of the medical pathology to the known position.

28. The method recited in claim 27 wherein the acoustically reflective object comprises an acoustically reflective seed, the method further comprising depositing the acoustically reflective seed into the tissue.

29. The method recited in claim 27 wherein the acoustically reflective object comprises a natural object within a body that comprises the tissue.

30. The method recited in claim 20 wherein changing the temperature of the tissue comprises insonifying the tissue with sufficient energy to effect changing the temperature.

31. The method recited in claim 20 further comprising inserting an interstitial needle within the tissue.

32. The method recited in claim 31 wherein:
the interstitial needle includes an acoustic emitter; and
localizing the portion of the medical pathology comprises:
    activating the acoustic emitter;
    identifying a position of the acoustic emitter from at least one of the first and second sets of received acoustic signals; and
    correlating the position of the emitter with a relative position of the medical pathology.

33. The method recited in claim 31 wherein:
the interstitial needle includes a thermocouple; and
changing the temperature of the tissue comprises activating the thermocouple.

34. The method recited in claim 31 wherein the interstitial needle is adapted to ablate tissue, the method further comprising ablating the medical pathology with the interstitial needle.

35. The method recited in claim 34 wherein the interstitial needle is adapted to ablate tissue cryogenically.

36. The method recited in claim 34 wherein the interstitial needle is adapted to ablate tissue through microwave irradiation of the tissue.

37. The method recited in claim 20 further comprising:
receiving a third set of acoustic signals scattered by the tissue after insonifying the medical pathology to localize a remaining portion of the medical pathology; and
thereafter, insonifying the remaining portion of the medical pathology with sufficient energy to damage the remaining portion of the medical pathology.

38. The method recited in claim 37 further comprising changing a temperature of the tissue after insonifying the medical pathology and prior to receiving the third set of acoustic signals.

39. A system for treating a medical pathology, comprising:
an array of transducers having a plurality of acoustic sources and a plurality of acoustic sensors, wherein the array is configured to be positioned such that the acoustic sensors receive acoustic radiation emitted from the acoustic sources and propagated through a volume of tissue containing at least a portion of the medical pathology, to thereby measure the speed of sound through the tissue;
means for changing the temperature of the tissue; and
a processing system programmed to:
    process information representative of the received acoustic radiation and generate an acoustic image of the tissue;
    simulate propagation of a divergent acoustic wave from a source positioned at a location of the portion of the medical pathology;
    determine an intensity of the simulated divergent acoustic wave at locations of the transmitters; and
    activate the transmitters to produce a corresponding acoustic wave convergent on the location of the portion of the medical pathology.

40. The system of claim 39, wherein the processing system is further programmed to localize the portion of the medical pathology from multiple sets of received acoustic radiation, wherein localizing the portion of the medical pathology comprises identifying the medical pathology from differences in at least first and second sets of received acoustic radiation, each of the at least first and second sets of received acoustic radiation being received when the portion of the medical pathology is at a different temperature.

41. The system of claim 39, wherein the processing system is further programmed to localize the portion of the medical pathology by correlating a known position of an acoustically reflective object proximate the medical pathology with a relative position of the medical pathology.

42. The system of claim 39, wherein the processing system is further programmed to localize the portion of the medical pathology by correlating a known position of an acoustically reflective seed proximate the medical pathology with a relative position of the medical pathology.

43. The system of claim 39, wherein the processing system is further programmed to localize the portion of the medical pathology by correlating a known position of a natural object proximate the medical pathology with a relative position of the medical pathology.

44. The system of claim 39, wherein the array of transducers comprises a ring transducer assembly.

45. The system of claim 39, wherein the array of transducers comprises a paddle transducer assembly.

46. The system of claim 45, wherein the paddle transducer assembly comprises acoustically-coupling pliable bladders adapted to be disposed to surround the tissue.

47. The system of claim 39, wherein the means for changing the temperature of the volume of tissue comprises means for insonifying the volume of tissue with sufficient energy to effect changing the temperature.

48. The system of claim 39, further comprising means for emitting acoustic radiation from within the tissue.

49. The system of claim 48, wherein the means for emitting acoustic radiation from within the tissue comprises an interstitial needle.

50. The system of claim 39, further comprising means for delivering therapy via a probe inserted into the tissue.

51. The system of claim 39, further comprising means for delivering pharmacological therapy to at least a portion of the tissue.

52. The system of claim 51, wherein the pharmacological therapy comprises micro-bubbles for containing the pharmacological therapy, and wherein the micro-bubbles are adapted to be fractured by the application of sufficient acoustic radiation from the transmitting system.

53. The method of claim 20, wherein changing a temperature of the volume of tissue includes changing a texture of the volume of tissue and wherein the differences in the first and second sets of received acoustic radiation result from changes in attenuation of the sound through the volume of tissue.

54. The method of claim 53, further comprising:
receiving subsequent sets of acoustic radiation transmitted through the volume of tissue; and
using each subsequent set of received acoustic radiation to determine whether to further insonify the portion of the medical pathology.

* * * * *